(12) United States Patent
Potter, Jr. et al.

(10) Patent No.: US 11,241,334 B2
(45) Date of Patent: Feb. 8, 2022

(54) SONIC AND ULTRASONIC CONTACT LENS APPARATUS

(71) Applicant: Visionage Therapies, LLC, New Haven, CT (US)

(72) Inventors: Mark W. Potter, Jr., New Haven, CT (US); Christopher Teng, New Haven, CT (US)

(73) Assignee: Visionage Therapies, LLC, New Haven, CT (US)

( * ) Notice: Subject to any disclaimer, the term of this patent is extended or adjusted under 35 U.S.C. 154(b) by 0 days.

(21) Appl. No.: 15/272,970

(22) Filed: Sep. 22, 2016

(65) Prior Publication Data
US 2017/0087014 A1 Mar. 30, 2017

Related U.S. Application Data

(60) Provisional application No. 62/222,999, filed on Sep. 24, 2015.

(51) Int. Cl.
*A61F 9/007* (2006.01)
*A61N 7/00* (2006.01)
*G02C 7/04* (2006.01)

(52) U.S. Cl.
CPC ...... *A61F 9/00745* (2013.01); *A61F 9/00781* (2013.01); *A61N 7/00* (2013.01);
(Continued)

(58) Field of Classification Search
CPC ... A61F 9/00745; A61F 9/00781; A61N 7/00; A61N 9/00745; A61N 9/00781; G02C 7/04; G02C 2202/10
See application file for complete search history.

(56) References Cited

U.S. PATENT DOCUMENTS 4,293,732 A * 10/1981 Rancourt ............ C03C 17/3417
                                                    136/256
9,259,597 B2    2/2016 Romano et al.
(Continued)

FOREIGN PATENT DOCUMENTS

WO     2009103721 A1    8/2009
WO     2013120020 A2    8/2013

OTHER PUBLICATIONS

Miller et al.; Overview of Therapeutic Ultrasound Applications and Safety Considerations; published on Apr. 1, 2012; Journal of Ultrasound in Medicine; vol. 31 Issue 4; pp. 623-634 (Year: 2012).*
(Continued)

*Primary Examiner* — Rochelle D Turchen
*Assistant Examiner* — Chao Sheng
(74) *Attorney, Agent, or Firm* — Wiggin and Dana LLP; Gregory S. Rosenblatt

(57) ABSTRACT

Disclosed are methods and apparatus, including eyewear and a contact lens, for delivering sound energy to an eye, comprising two or more sonic or ultrasonic transducers that emit sound energy, wherein each transducer is (i) operably linked to a power source and (b) capable of emitting sound energy at more than one frequency and for a variable time period; and a positioning mechanism to position the transducers at an exterior surface of an eye so as to deliver sound energy to an internal part of the eye, for example the Schlemm's canal or trabecular meshwork.

16 Claims, 28 Drawing Sheets

(52) U.S. Cl.
CPC ........ *A61N 2007/0073* (2013.01); *G02C 7/04* (2013.01); *G02C 2202/10* (2013.01)

(56) References Cited

U.S. PATENT DOCUMENTS

| | | | |
|---|---|---|---|
| 9,884,180 B1* | 2/2018 | Ho | A61N 1/0543 |
| 10,025,118 B1* | 7/2018 | Markus | G02C 7/04 |
| 2002/0010458 A1 | 1/2002 | Urich et al. | |
| 2004/0030269 A1 | 2/2004 | Horn et al. | |
| 2006/0074355 A1* | 4/2006 | Slayton | A61H 23/0245 |
| | | | 601/2 |
| 2008/0051681 A1 | 2/2008 | Schwartz | |
| 2008/0275370 A1 | 11/2008 | McIntyre et al. | |
| 2009/0192437 A1 | 7/2009 | Soltz et al. | |
| 2010/0179425 A1* | 7/2010 | Zadicario | A61B 8/0816 |
| | | | 600/438 |
| 2010/0275985 A1* | 11/2010 | Zheng | H01L 51/4266 |
| | | | 136/256 |
| 2011/0009779 A1* | 1/2011 | Romano | A61F 9/00745 |
| | | | 601/2 |
| 2011/0087138 A1 | 4/2011 | Kahook | |
| 2012/0162600 A1* | 6/2012 | Pugh | A61F 2/1624 |
| | | | 351/159.03 |
| 2012/0236524 A1* | 9/2012 | Pugh | G02B 1/043 |
| | | | 361/783 |
| 2013/0211389 A1 | 8/2013 | Chuck et al. | |
| 2013/0211395 A1* | 8/2013 | Schwartz | A61F 9/00745 |
| | | | 606/28 |
| 2013/0245505 A1 | 9/2013 | Khuri-Yakub et al. | |
| 2013/0289545 A1 | 10/2013 | Baerveldt et al. | |
| 2014/0243645 A1* | 8/2014 | Leonardi | A61B 5/0002 |
| | | | 600/398 |
| 2014/0364780 A1 | 12/2014 | Kahook | |
| 2015/0005606 A1* | 1/2015 | Honore | A61B 5/14532 |
| | | | 600/365 |
| 2015/0063605 A1 | 3/2015 | Pugh | |
| 2015/0100001 A1 | 4/2015 | Bujak | |
| 2015/0201837 A1* | 7/2015 | Song | A61B 5/0002 |
| | | | 600/345 |
| 2017/0042480 A1* | 2/2017 | Gandhi | G02C 7/04 |

OTHER PUBLICATIONS

Sterk et al.; The effect of therapeutic ultrasound on the average of multiple intraocular pressures throughout the day in therapy-resistant glaucoma; Graefe's Archive for Clinical Experimental Ophthalmology 227, pp. 36-38 (Year: 1989).*
Friedman, David S et al., Prevelance of open-angle glaucoma among adults in the United States, Arch Ophthalmol, 122:532-538, Apr. 2004.
Ghorayeb, RS et al., Biophysical characterization of low-frequency ultrasound interaction with dental pulp stem cells. Journal of Therapeutic Ultrasound 2013 1:12, 10 pages.
Grierson, I. & Chisolm, IA, Clearance of debris from the iris through the drainage angle of the rabbit's eye, British Journal of Ophthalmology, 1978, 62:694-704.
Mansberger, SL et al, Reduction in intraocular pressure after cataract extraction: the ocular hypertension treatment study, Ophthalmology, 2012, 119:1826-1831.
Mantravadi AV & Vadhar, N, Glaucoma, Prim Care Clin Office Pract 2015, 42:437-449.
Quigley, HA, Number of people with glaucoma worldwide, British Journal of Ophthalmology, 1996, 80:389-393.
Regar, E et al., Sonotherapy, antirestenotic therapeutic ultrasound in coronary arteries: the first clinical experience, Catheterization and Cardiovascular Interventions, 2003, 60:9-17.
Shingleton, BJ et al., Three and five year changes in intraocular pressures after clear corneal phacoemulsification in open angle glaucoma patients, glaucoma suspects, and normal patients, J Glaucoma, 2006, 15(6):494-498.
PCT International Search Report and Written Opinion in PCT/US16/53264, dated Dec. 9, 2016, 9 pages.

* cited by examiner

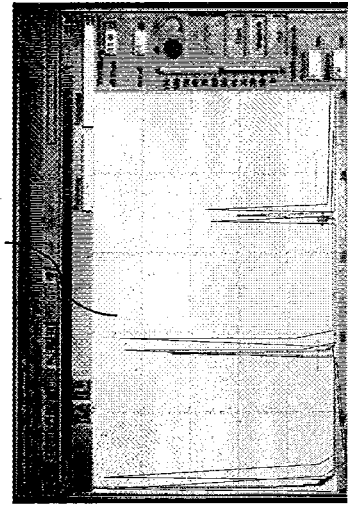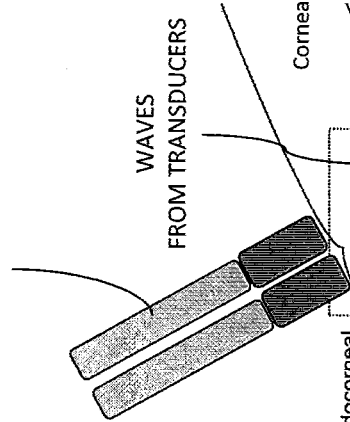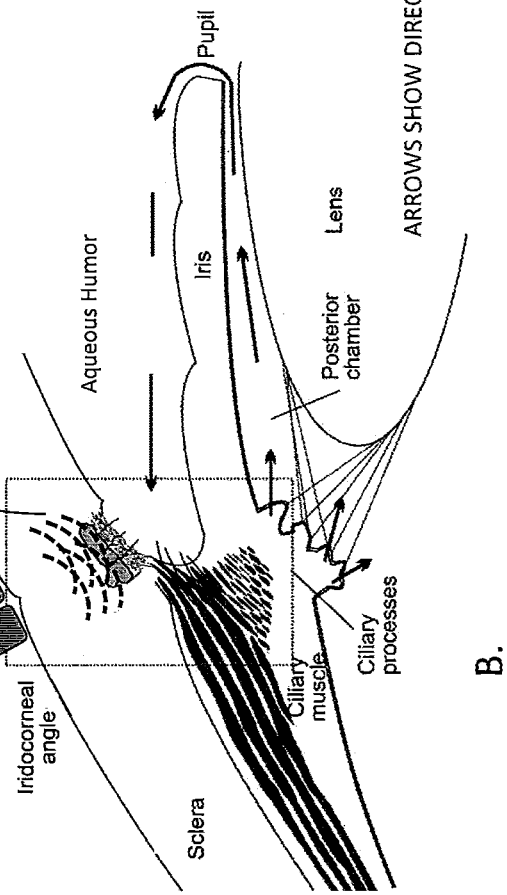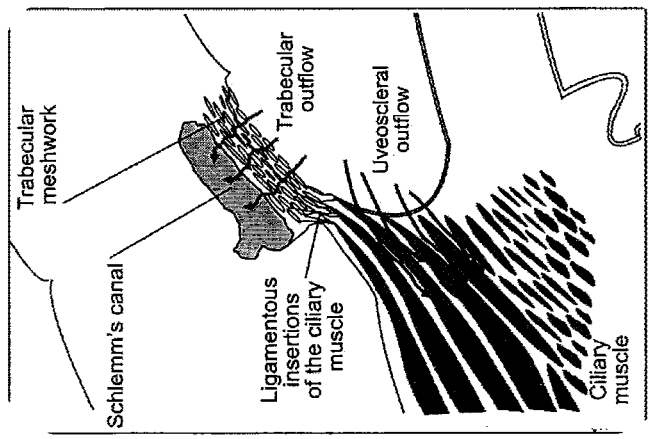
Figs. 2A-2C

SAMSUNG GearBlink®
SMART CONTACT LENS
B.

GOOGLE and NOVARTIS, Contact
Lens MEASURES BLOOD SUGAR
D.

SENSI-MED Triggerfish® MEASURES
INTRAOCULAR PRESSURE
A.

Babak Parviz, BIONIC EYESIGHT
PROTOTYPE CONTACT LENS
C.

SONIC AND ULTRASONIC CONTACT LENS APPARATUS

CROSS-REFERENCE TO RELATED APPLICATIONS

This application claims the benefit under 35 U.S.C. § 119(e) to U.S. Provisional Application No. 62/222,999, filed Sep. 24, 2015, the contents of which are incorporated herein by reference in their entirety.

FIELD OF THE DISCLOSURE

Disclosed are devices for non-invasive delivery of sonic and ultrasonic energy to an eye, and methods of using such devices for the treatment of glaucoma.

BACKGROUND OF THE DISCLOSURE

Glaucoma is the leading cause of irreversible blindness and the second leading cause of blindness in the world. There are 67 million people affected by glaucoma worldwide (10% suffer complete blindness), projected to increase to 80 million by 2020. Three percent of the global population over 40 years old, and 1 in 10 over the age of 80, has glaucoma. In the United States, 2.2 million people have chronic open angle glaucoma (COAG), projected to increase to 3.4 million by 2020. (Quigley H A, *Br J Ophthalmol*, 1996; Friedman D S, et al., *Arch Ophthalmol*, 2004)

The glaucoma medication market is expected to rise from $2.4 billion in 2013 to $3 billion by 2023 across the major markets of the United States, France, Germany, Italy, Spain, the United Kingdom and Japan. Medication sales are expected to increase from $1.7 billion in 2013 to $2.2 billion by 2023.

Types of glaucoma include open and closed angle glaucoma, pigmentary glaucoma and exfoliation glaucoma. In most types of glaucoma, blindness is a result of damage to the optic nerve caused by increased fluid pressure inside of the eye, or increased intraocular pressure (IOP). The trabecular meshwork (TM) is series of cellular filters, admitting fluid from the anterior eye into its primary drain, the Schlemm's canal. This meshwork has three layers of cells, each with apertures that are progressively smaller. Primary resistance to fluid outflow is at the juxtacanalicular TM and the inner wall of the Schlemm's canal. While the TM does a very good job of keeping pigment and cellular debris out of the Schlemm's canal, and vessels that drain the Schlemm's canal into the body's lymphatic system, the TM is vulnerable to clogging by cellular debris consisting primarily of melanocytes, melanin granules, and other debris from the iris and the interior of the eye. The uveal meshwork is the first and coarsest meshwork to guard this drain and has the widest apertures for fluid and debris to pass through, but in the case of many advanced glaucoma patients even this becomes completely clogged by an agglomeration of waste and dead cells.

There is currently no cure for glaucoma. Medical treatments are directed at decreasing intraocular pressure on an ongoing basis as needed to limit or slow the progression of damage to the optic nerve and preserve the patient's vision. Current glaucoma medications face several barriers to patient compliance including cost, side effects, difficult administration, comorbid eye disease, patient age, education or income, frequency of dosing, and multiple medications. Early clinical intervention for glaucoma includes topical pharmaceutical agents (such as medicated eye drops) and laser treatment. Intraocular surgical procedures, such as filtering surgery trabeculectomy and tube implant surgery, are available but generally reserved for patients for whom topical medications and laser treatment have not been successful. Topical medications such as eye drops are expensive, must be frequently dosed and are difficult to administer resulting in poor compliance. Many new surgeries are being developed to lower intraocular pressure in glaucoma patients, including microinvasive glaucoma surgery (MIGS) such as iStent, trabectome, endocyclophotocoagulation, hydrus microstent, cypass (suprachoroidal) and xen implant (anterior chamber), however, any invasive procedure will carry risks of infection, pain, scarring and other adverse complications.

There have been attempts to design non-invasive devices that deliver ultrasonic energy to the eye to lower intraocular pressure in glaucoma patients. For example, United States Patent Application Publication Nos. US 2014/0364780, US 2011/0087138, US 2013/0211395 and US 2008/0051681 disclose methods for reducing intraocular pressure using devices that emit ultrasonic energy at the surface of the eye to oscillate the trabecular meshwork or Schlemm's canal. However, the disclosed devices are hand-held devices that are placed in contact with the surface of the eye. Hand-held devices lack the accuracy needed to repeatedly administer ultrasonic energy to the precise location at the surface of the eye. Also, a clinician would need to be involved to hold the device at the correct location and angle, thus increasing the cost of treatment. Furthermore, the disclosed devices comprise a single transducer that does not permit the delivery of a combination of frequencies or the delivery of frequencies in formats that would minimize tissue damage, such as phased array. United States Patent Application Publication Nos. US 2014/0364780, US 2011/0087138, US 2013/0211395 and US 2008/0051681 are incorporated by reference herein in their entireties.

In short, there is a need for non-invasive methods and devices to effectively administer glaucoma treatments that do not damage the tissue of the eye, and that can be accurately performed on a repeated basis as needed to decrease intraocular pressure in a patient's eye, and preferably, with minimal supervision by a clinician.

BRIEF SUMMARY

Disclosed herein is an apparatus for delivering sound energy to an eye, comprising: (a) two or more transducers that emit sound energy and are operably linked to a power source, wherein each transducer is independently capable of emitting sound energy at more than one frequency and for a variable time period; and (b) a positioning mechanism to position the transducers at an exterior surface of an eye so as to deliver the sound energy to an internal part of the eye.

Also disclosed herein is an eyewear apparatus for delivering sound energy to an eye, comprising: (a) two or more sound transducers operably linked to a power source, mounted directly or indirectly to an eyewear, that emit sound energy, wherein each transducer is capable of emitting sound energy at more than one frequency and for a variable time period; and (b) a positioning mechanism, mounted directly or indirectly to the eyewear apparatus, to position the transducers at an exterior surface of an eye so as to deliver the sound energy to an internal part of the eye. In some embodiments, the eyewear apparatus is selected from the group consisting of: glasses, goggles, a helmet, and a visor.

Also disclosed herein is a contact lens for delivering sound energy to an eye, comprising: two or more sound transducers that emit sound energy and are operably linked to a power source, wherein each transducer is integrated into the contact lens and independently capable of emitting sound energy at more than one frequency and for a variable time period, wherein the transducers are positioned at the corneal surface of the eye so as to deliver the sound energy to a desired internal part of the eye. In some embodiments, the contact lens consists of from 4 to 24 transducers.

In some embodiments, the sound energy comprises sonic frequencies, for example, high sonic frequencies, or ultrasonic frequencies, for example low or high ultrasonic frequencies. In some embodiments, the sound energy is selected from a frequency consisting of: from about 20 kilohertz to about 200 kilohertz, about 5 kilohertz to about 200 kilohertz, about 5 kilohertz to about 50 kilohertz, and about 5 kilohertz to about 25 kilohertz.

In some embodiments, the variable time period is selected from the group consisting of: about 0.1 second, about 0.5 seconds, about 1 second, about 2 seconds, about 5 seconds, about 10 seconds, about 15 seconds, about 20 seconds, about 25 seconds, and about 30 seconds.

In some embodiments, the transducers emit sound energy in a phased array format. In some embodiments, the transducers are positioned on a ring or on a rotor.

In some embodiments, the positioning mechanism is selected from the group consisting of: self-adjustable, manually adjustable, electronically adjustable, and any combination thereof. In some embodiments, the positioning mechanism comprises a multiple-axis suspension system. In some embodiments, the positioning mechanism comprises a 3- or 4-axis gimbal mount.

In some embodiments, the internal part of the eye is selected from the group consisting of: the Schlemm's canal, trabecular meshwork, and both the Schlemm's canal and trabecular meshwork. In some embodiments, the internal part of the eye is an area surrounding the Schlemm's canal or the trabecular network. In some embodiments, the exterior surface of the eye is the cornea. In some embodiments, the sound energy is delivered axially or radially at the exterior surface of the eye.

In some embodiments, the apparatus is operably linked to a computer interface.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention will be apparent from the following detailed description taken in conjunction with the accompanying drawings.

FIGS. 2A-2C illustrate an embodiment of a transducer array over the indocorneal angle in close-up section (A), the positioning of the array over the junction of cornea and sclera (B), and feedback from the transducer array as it may appear on the system monitor (C).

DETAILED DESCRIPTION

Glaucoma is progressive optic neuropathy characterized by loss of retinal ganglion cells resulting in visual field (VF) loss. The primary cause of glaucomatous nerve damage is a build-up in intraocular pressure (IOP) of fluid in the anterior chamber of the eye. The pressure builds because the eye produces fluid more quickly than it can drain through the trabecular meshwork (TM) and Schlemm's canal. In most cases, this is due to a fouling of the TM, otherwise an effective filter and pressure maintenance system for fluid leaving the eye. The non-invasive methods and devices described herein are based on the use of ultrasonic or sonic vibrations to loosen the meshwork, destroy debris clogging the TM, promote outflow to of intraocular fluid to the Schlemm's canal and lower intraocular pressure.

Figure 1:
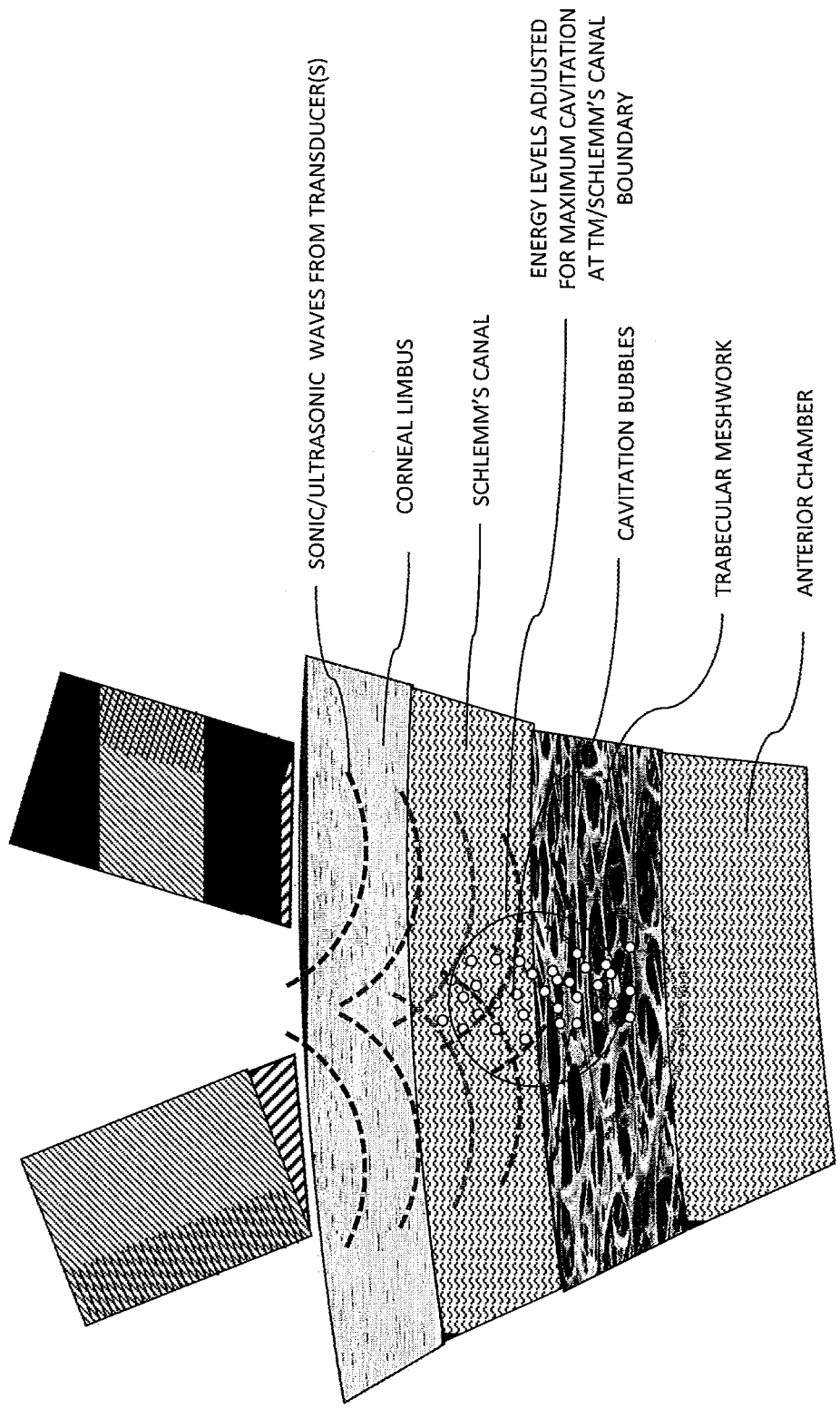
FIG. 1 illustrates in schematic section view, an embodiment of a two-transducer array applying cavitation energy to an area above the Schlemm's canal and trabecular meshwork.

FIG. 1 illustrates in schematic section view, an embodiment of a two-transducer array applying cavitation energy at an intocorneal angle to an area above the Schlemm's canal and trabecular meshwork. Sonic and ultrasonic waves from the transducers travel through the corneal limbus to target precise locations in the interior of the eye. The energy beams are targeted to a precise location to form cavitation bubbles in the Schlemm's canal and the TM. Energy levels, direction, frequency and phase are adjusted for maximum cavitation at the boundary of the Schlemm's canal and TM. Individual beam energies attenuate to a harmless level. Overlapping nodes cavitate fluids and clean the TM. Wave amplitudes are adjusted to target fluid in the Schlemm's canal. Heat beneath the transducers is mitigated, while phase and frequency modulation shifts the location of wave hot spots.

FIG. 2 illustrates a method to prevent cavitation of the tear layer of the eye or burning of corneal cells using a single transducer array. FIG. 2A shows the anatomy of the indocorneal angle in close-up section with arrows showing the direction of fluid flow in the eye. FIG. 2B illustrates the positioning of two adjustable phased array multiple transducers over the junction of the cornea and sclera and providing stimulation at the indocorneal angle. Lower wattage from two or more sources reduces the risk of injury to the eye. Phase adjustment ensures that cavitation is distributed evenly through the targeted area and refraction combines power in precisely defined areas. FIG. 2C shows echoes from the phased array and feedback from the transducer array as it may appear on an operably linked system monitor.

Figures 3A, 3B:
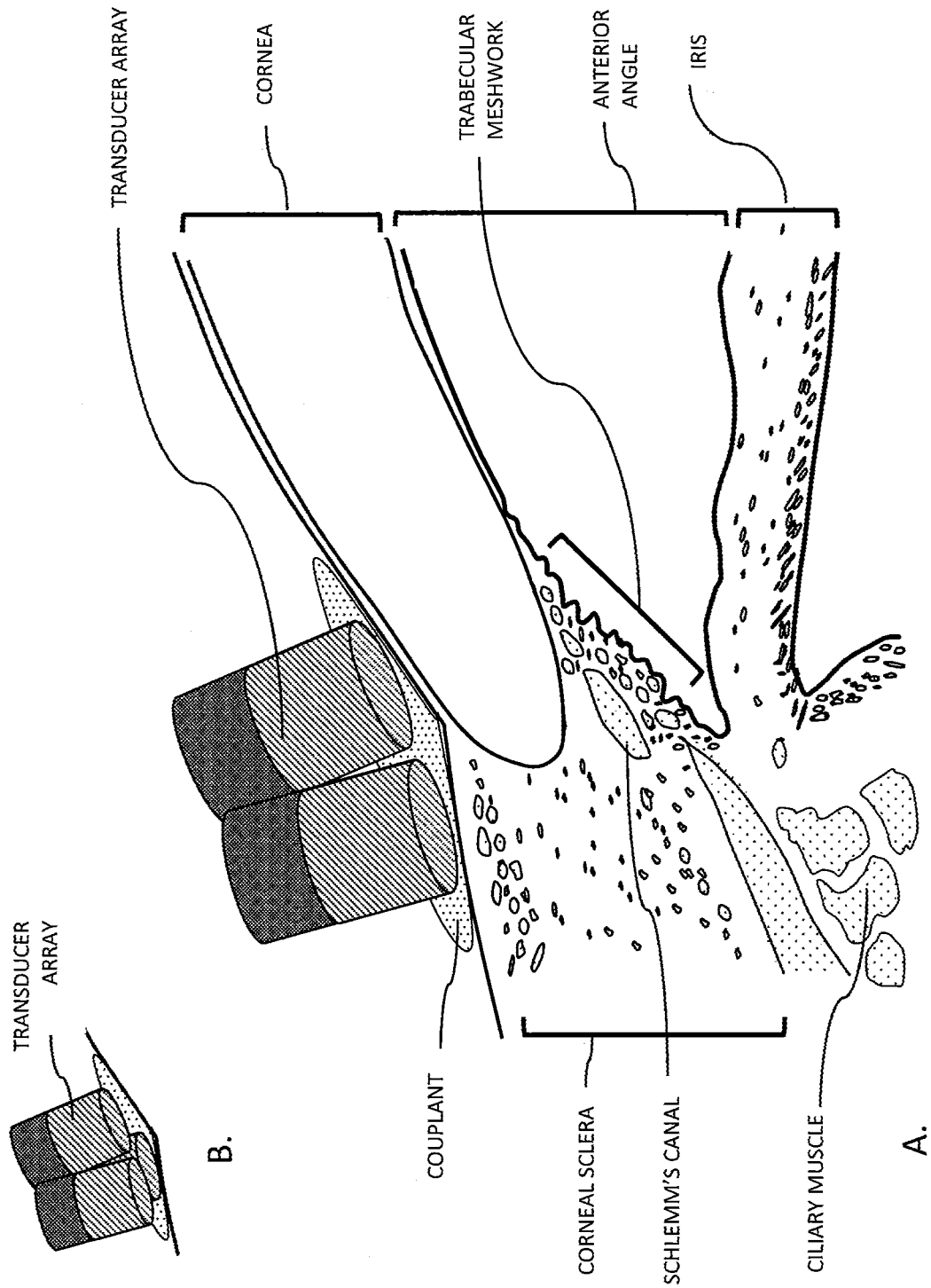
FIGS. 3A-3B shows an embodiment of a transducer array positioned over the indocorneal angle, with design adjusted in angle to match the exterior junction of cornea and sclera, with two transducers visible (A), and a close-up of a configuration with three transducers (B).

FIG. 3 shows an embodiment of a transducer array with two transducers positioned over the indocorneal angle, with design adjusted in angle to match the exterior junction of cornea and sclera (or corneal sclera), with two transducers illustrated. Couplant is introduced at the surface of the eye where the transducers are placed. Interior structures of the eye are also shown (Schlemm's canal, ciliary muscle, TM, and iris). FIG. 3B shows a close-up of a transducer array configuration with three transducers illustrating that matching the exterior angle junction is preferred and may be necessary when using the highest frequency ranges of ultrasonic stimulation. For rotating transducer arrays it may not be necessary to consider the exterior angle junction because in some embodiments, couplant, or the pliability of the eye surface may minimize the need for such design adjustments, however for higher frequency cavitation, particularly where the desired energy, is to propagate through the cornea as well as the sclera, an angle-adjusted transducer array may be preferred.

Figures 4A, 4B:
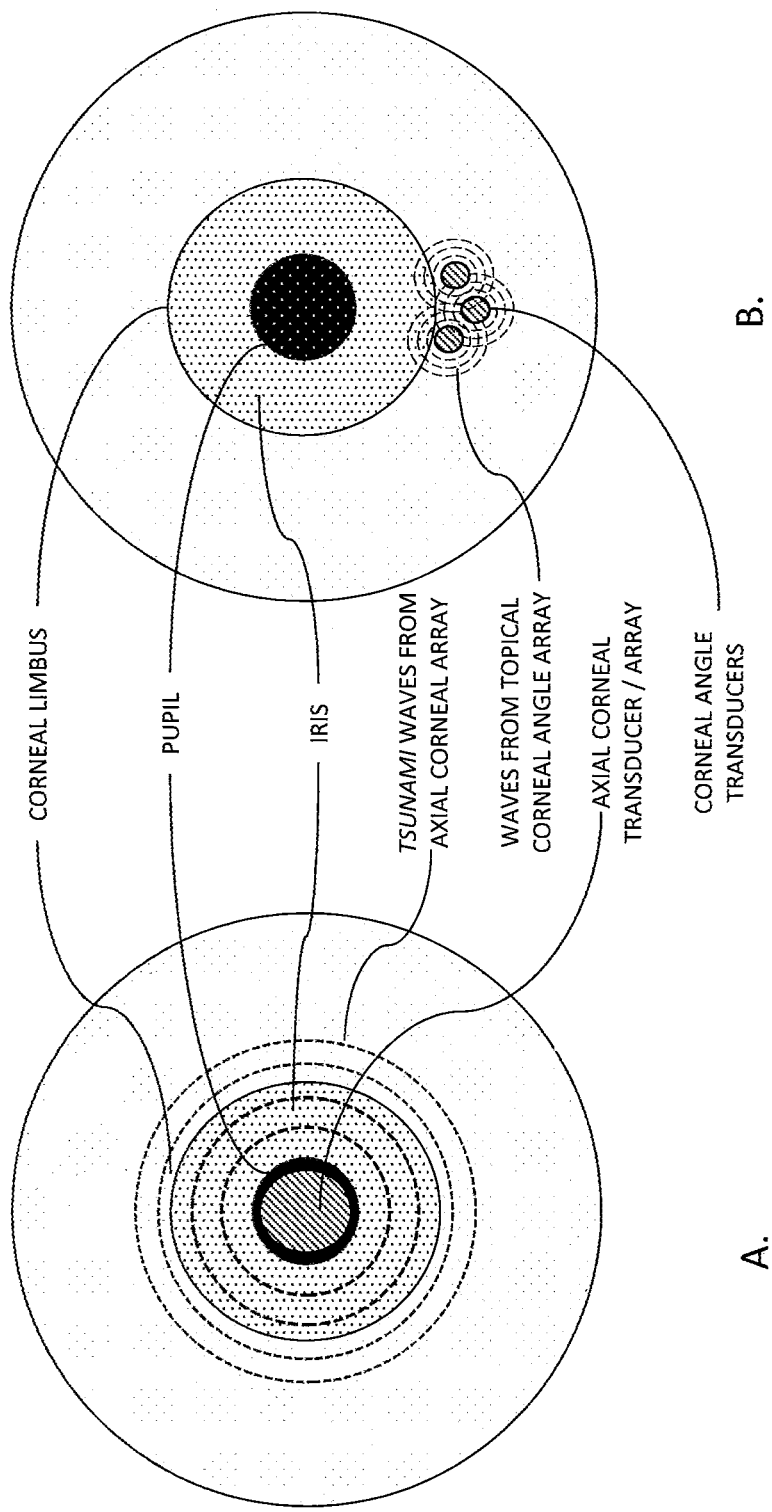
FIGS. 4A-4B illustrate an anterior view of the eye where topical axial stimulation is applied to the front of the cornea (A), or over the corneal angle (B).

FIG. 4 illustrates an anterior view of the eye where topical axial stimulation is applied to the eye at various positions in relation to the corneal limbus, pupil and iris. In FIG. 4A, the transducer is placed at the front and center of the cornea (corneal angle) front In FIG. 4B, a transducer array is placed over the corneal limbus (topical axial). Transducers and waves produced by the transducers are also depicted.

Figures 5A, 5B:
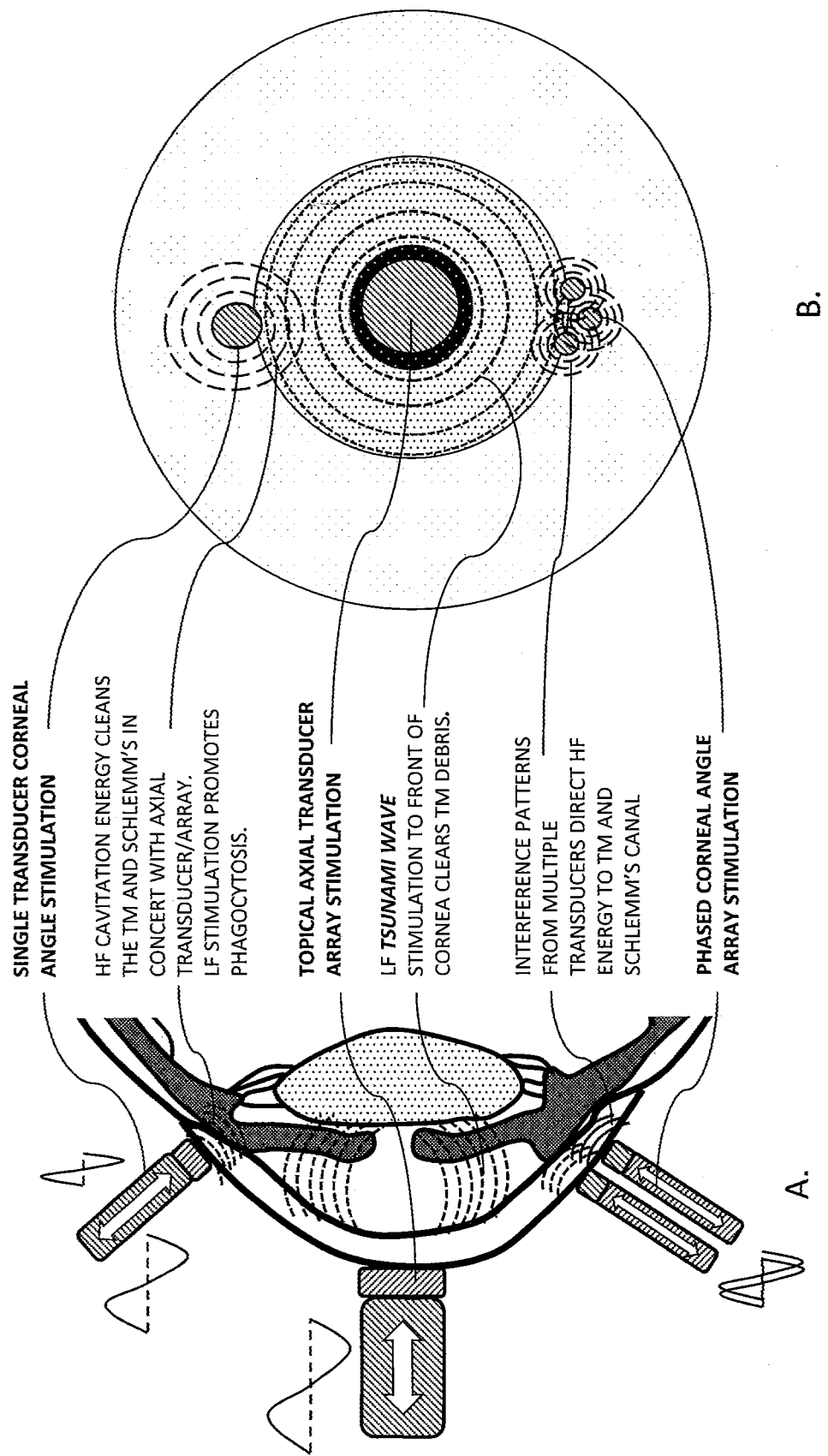
FIGS. 5A-5B show variations of simultaneous corneal angle and topical axial transducer stimulation, a sectional view with anterior eye anatomy (A), and an anterior view schematic (B).

FIG. 5 shows variations of simultaneous corneal angle and topical axial transducer stimulation, a sectional view with anterior eye anatomy (FIG. 5A), and an anterior view schematic (FIG. 5B). A single transducer applies topical high frequency (HF) ultrasound energy and cavitation cleans the TM and Schlemm's canal. Topical low frequency (LF) stimulation promotes phagocytosis. When the transducer is applied to the front of the cornea, tsunami waves transport energy to the circumference of the TM and Schlemm's canal. Phased array corneal stimulation interference patterns from multiple transducers direct energy to particular positions of the TM and Schlemm's canal. Topical axial stimulation propagates LF energies, which includes high sonic frequencies (HSF) around the full circumference of the TM, primarily in order to 'clear' debris broken up or dislodged by ultrasonic wavelengths. Except where noted the designations HF and LF refer to ultrasonic energies. Sonic wavelengths will have some positive affect, particularly in the mid and upper ranges (see Example 7).

Figure 6:
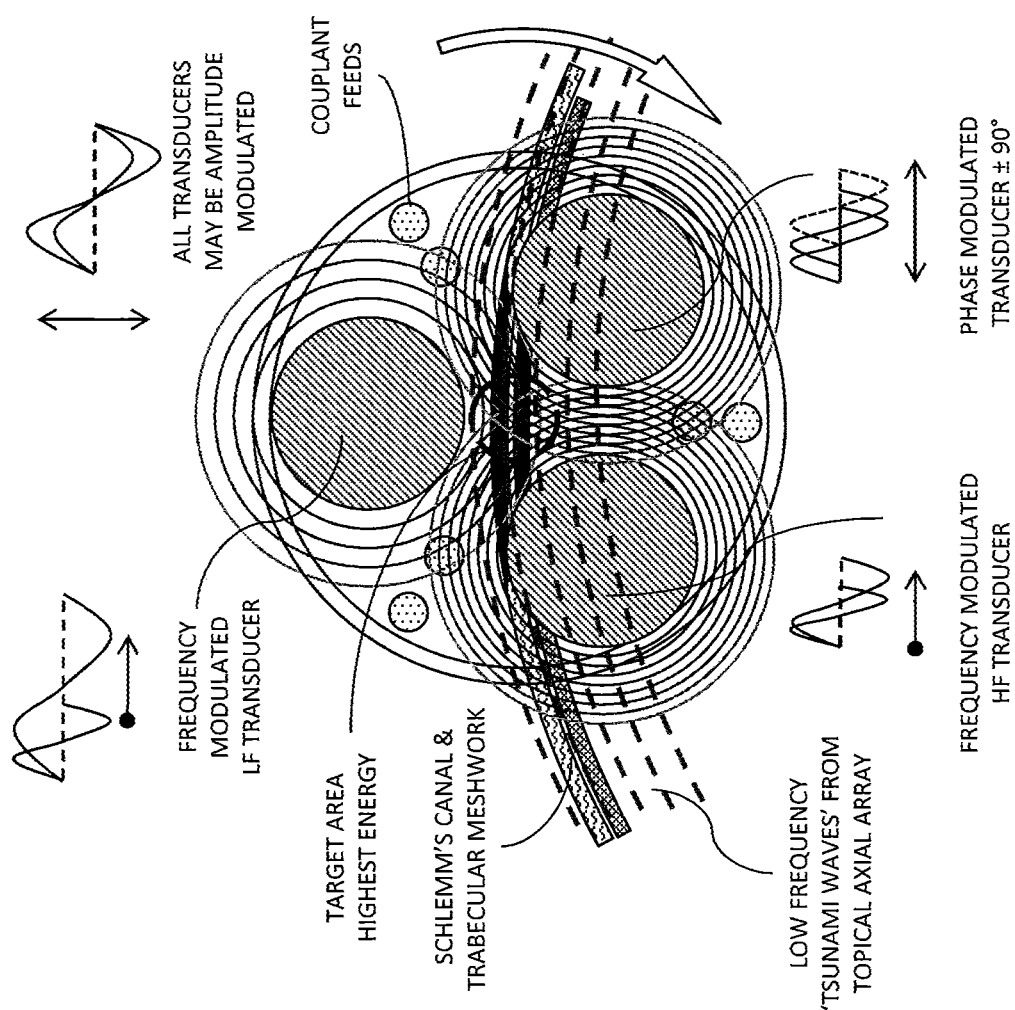
FIG. 6 shows a close-up schematic of the frequency product over an area of Schlemm's canal and the trabecular meshwork.

FIG. 6 shows a close-up schematic of the frequency product over an area of Schlemm's canal and the trabecular meshwork. A three-transducer array with couplant feeds is illustrated with the following three transducers: a frequency modulated LF transducer, a frequency modulated HF transducer and a phase modulated ±90° transducer. All of the transducers may be amplitude modulated. Low frequency tsunami waves from the topical axial array are shown around the Schlemm's canal and TM. The target area of highest energy is also shown.

Figures 7A, 7B:
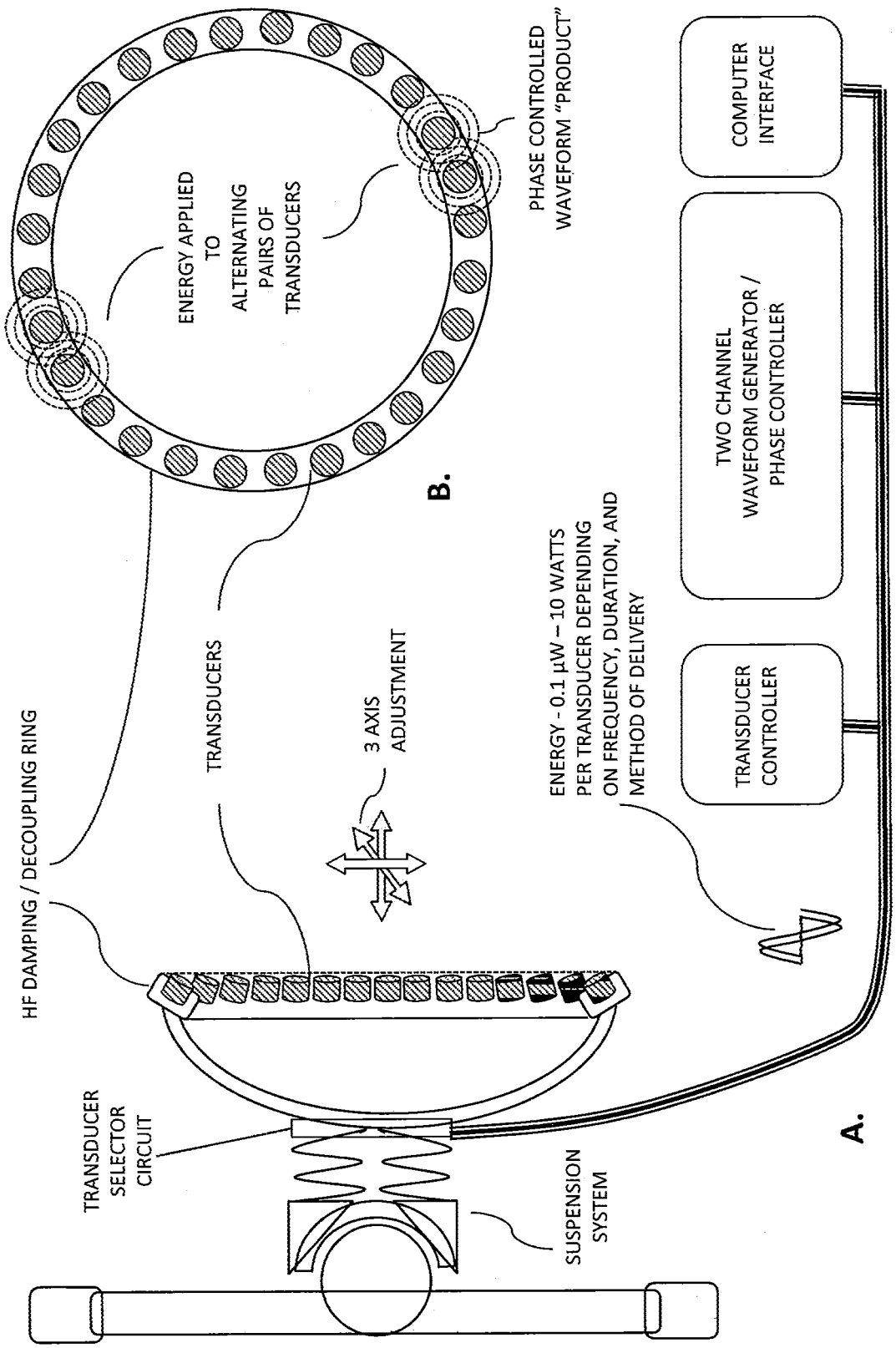
FIGS. 7A-7B illustrate embodiments of a transducer array ring, here shown in side-view schematic of a glaucoma glasses system (A), and a rear-view schematic of the transducer array ring (B), demonstrating how alternating pairs of transducers are energized around the eye.

FIG. 7 illustrates embodiments of a transducer array ring with suspension, here shown in side-view schematic of a glaucoma glasses system (FIG. 7A, also see Example 2), and a rear-view schematic of the transducer array ring (FIG. 7B), demonstrating how alternating pairs of transducers are energized around the eye. The suspension system and transducer selector circuit allow for customization of the position of the phased array ring via a three-axis adjustment and adjustment of the current (AC) applied to the transducers. The phased array ring is positioned between HF damping/decoupling rings. The transducer controller can supply energy (for example 0.1 microwatts-10 watts) per transducer depending on frequency and method of delivery of the sound energy, for example energy can be applied to alternating pairs of transducers to create a phase controlled waveform 'product.' A two channel waveform generator/phase controller and operably linked computer interface are also shown.

Figures 8A, 8B, 8C, 8D, 8E:
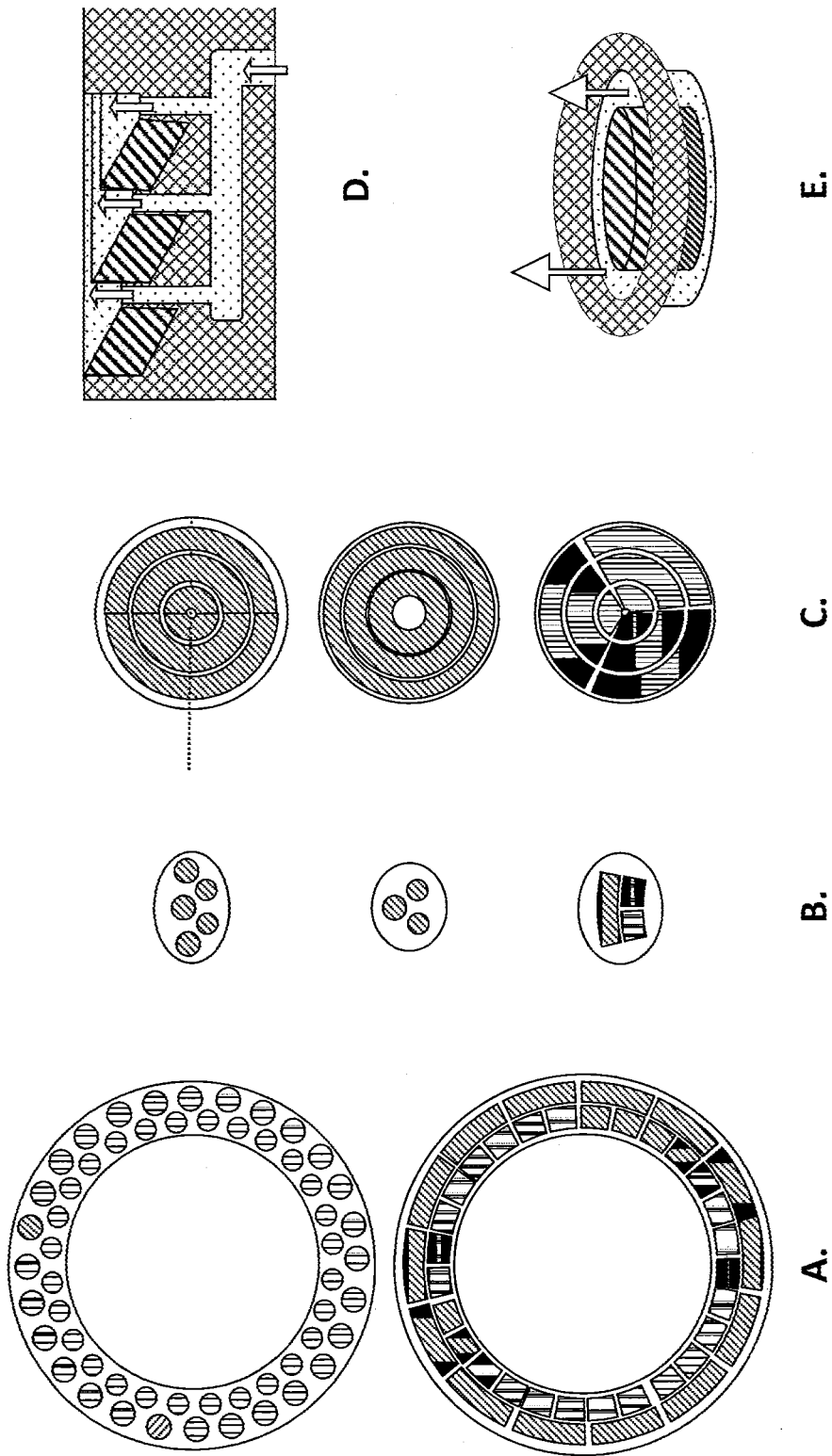
FIGS. 8A-8E illustrate embodiments of micro-machined ocular transducer arrays, rings for placement over the corneal limbus (A), fractional circumference arrays for use over portions of the corneal limbus (B), axial focused beam arrays for topical corneal use (C), a section of a fresnel array from with couplant slots (D), and an oblique view with couplant slots (E).

FIG. 8 illustrates various embodiments of micro-machined ocular transducer arrays, showing phased array rings for placement over the corneal limbus (FIG. 8A), fractional circumference arrays for use over portions of the corneal limbus (FIG. 8B), axial focused beam arrays for topical corneal use (FIG. 8C), a section of a fresnel array from with couplant slots (FIG. 8D), and an oblique view with couplant slots (FIG. 8E).

Figures 9A, 9B, 9C:
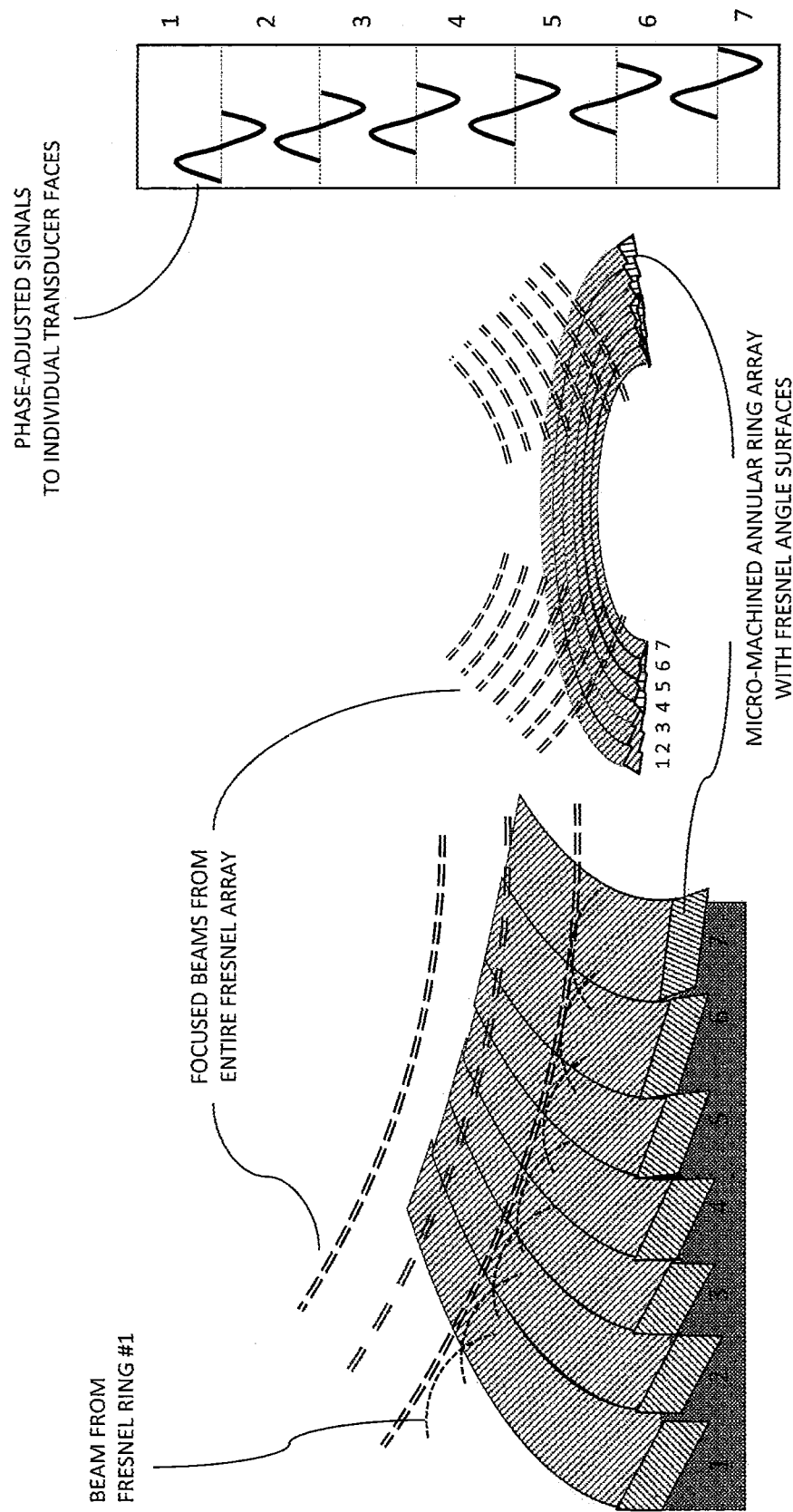
FIGS. 9A-9C illustrate embodiments of micro-machined transducer arrays, with a fresnel design (A), a semi-circular arrangement of such rings and the resulting wave product (B), each ring receiving one of seven phased signals (C) so as to produce a single focused wave-form.

FIG. 9 illustrates embodiments of a micro-machined annular ring array with Fresnel angle surfaces. Fresnel angles cut into individual transducer faces. This design conserves couplant and redirects and focuses energy at an oblique angle. The near field Fresnel zone is shortened. Signal phase delay for each transducer produces a combined wave. FIG. 9A shows an array with a seven-ring fresnel design showing a beam from Fresnel ring number 1. FIG. 9B shows a semi-circular arrangement of such rings and the resulting wave product. Focused beams are emitted from the entire fresnel array. FIG. 9C shows each ring receiving one of seven phased-adjusted signals to individual transducer faces so as to produce a single focused wave-form.

Figures 10A, 10B, 10C:
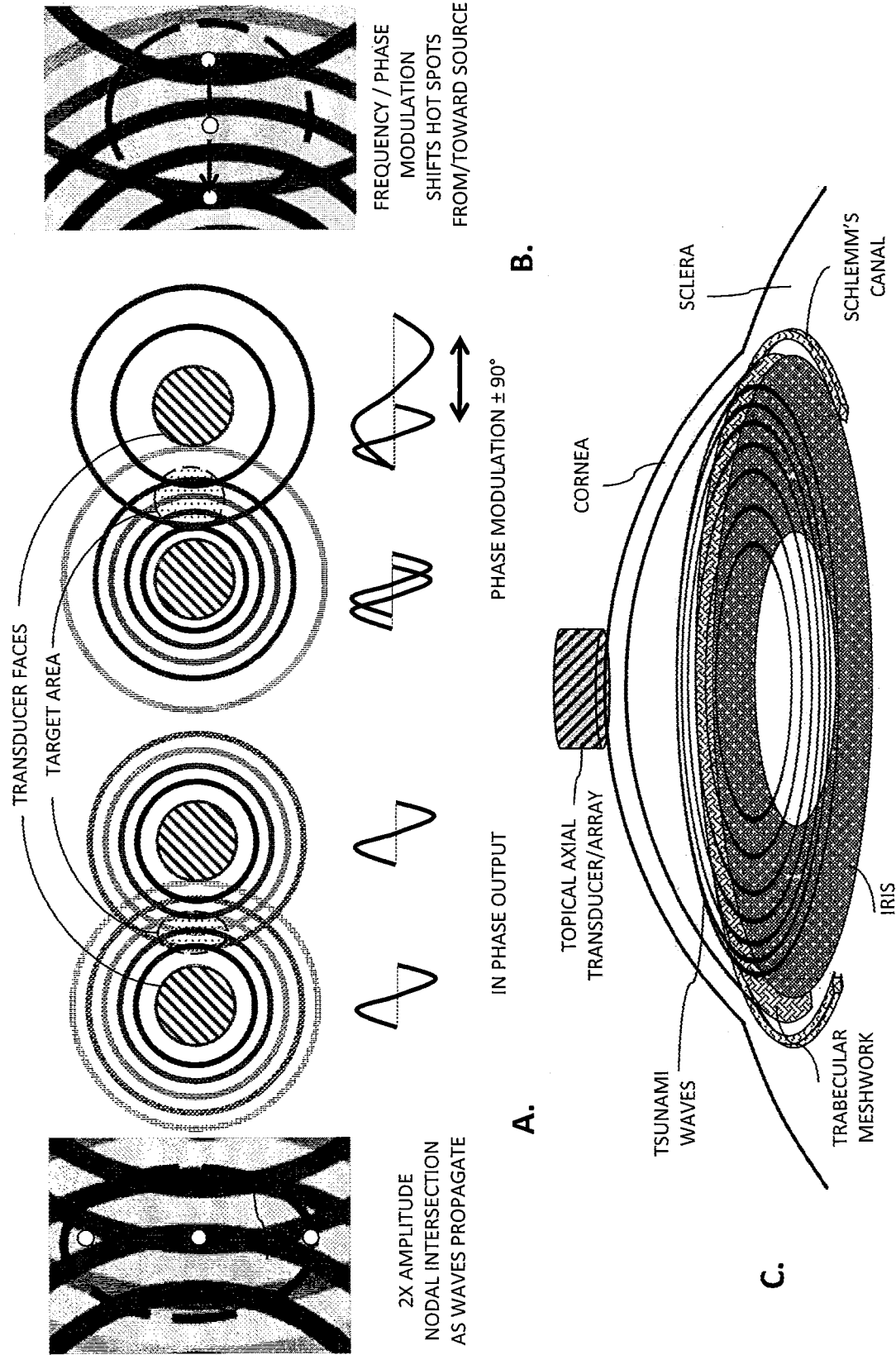
FIGS. 10A-10C depict the manner in which waves propagate, in particular how beams reinforce at nodal intersections (A), how phase and frequency modulation may be used to shift focus of target area by manipulating signal from one transducer (B), and how tsunami waves from a topical axial transducer decrease in wavelength and increase in amplitude at the shallower depths of the anterior eye (C).

FIG. 10 depicts the manner in which waves propagate. FIG. 10A illustrates how beams reinforce at nodal intersections with a 2× amplitude nodal intersection as waves propagate. FIG. 10B shows how phase and frequency modulation may be used to shift focus of target area by manipulating signal from one transducer. FIG. 10C illustrates how tsunami waves from a topical axial transducer/array applied at the cornea decrease in wavelength and increase in amplitude at the shallower depths of the anterior eye. Modulated phase/frequency eliminates single transducer hot spots that can damage the eye, and allow cavitation bubbles to build evenly throughout the target area. The zone of effect can be moved without damaging or burning the cornea. The phased output of transducers can be varied at ±90° to create wave cancellation, anti-nodes or reinforcement at nodes. With two transducers, the effect can cancel or double the effective energy. With three or more transducers, the target area can be more accurately defined. Frequency modulation evens out the combined effect. For three or more transducers both phase modulation and frequency modulation can be used to reduce hot spots.

Figures 11A, 11B, 11C:
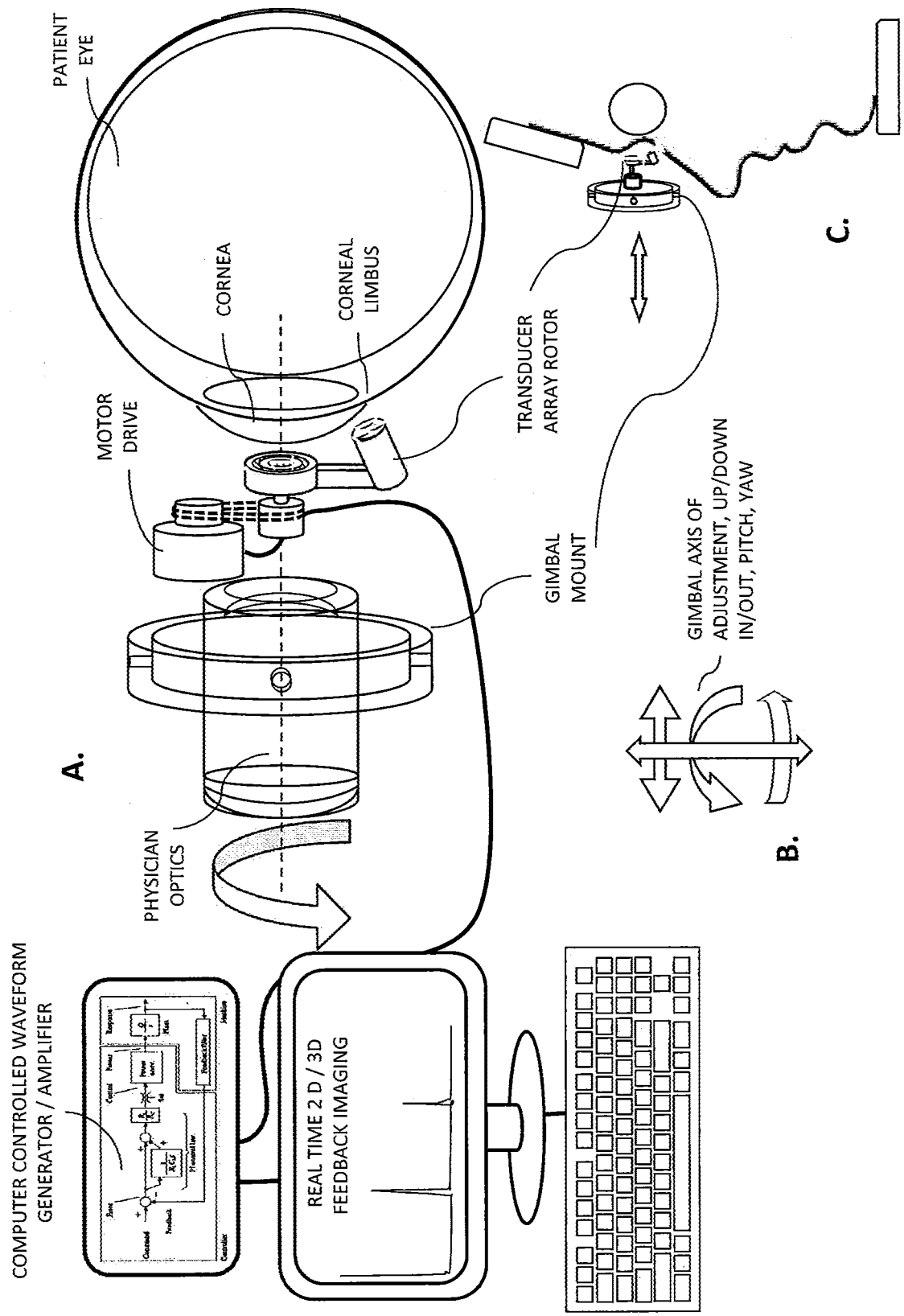
FIGS. 11A-11C illustrate an exploded oblique schematic view of an embodiment of the in-clinic device (A), axis of adjustment for the gimbal mount (B), and a schematic of the patient head positioned with the rotor in-line with the patient eye (C).

FIG. 11A illustrates an exploded oblique schematic view of an embodiment of the gimbal mounted phased transducer array (ring or rotor) with 4-axis controls as described for the in-clinic device (see Example 1). A motor drive and transducer array rotors positioned at the cornea and corneal limbus of the patient eye. The device has physician optics (for example, to watch for clouding of vitreous or scarring of the cornea) and is operably linked to a computer controlled waveform generator/amplifier and real-time 2D/3D feedback imaging and patient-specific therapy recordkeeping software. FIG. 11B shows the axis of adjustment for the gimbal mount which allow adjustments in/out, pitch, up/down and yaw right/left. FIG. 11C is a schematic of the patient head positioned with the rotor in-line with the patient eye using a chin rest and forehead restraint.

Figures 12A, 12B, 12C:
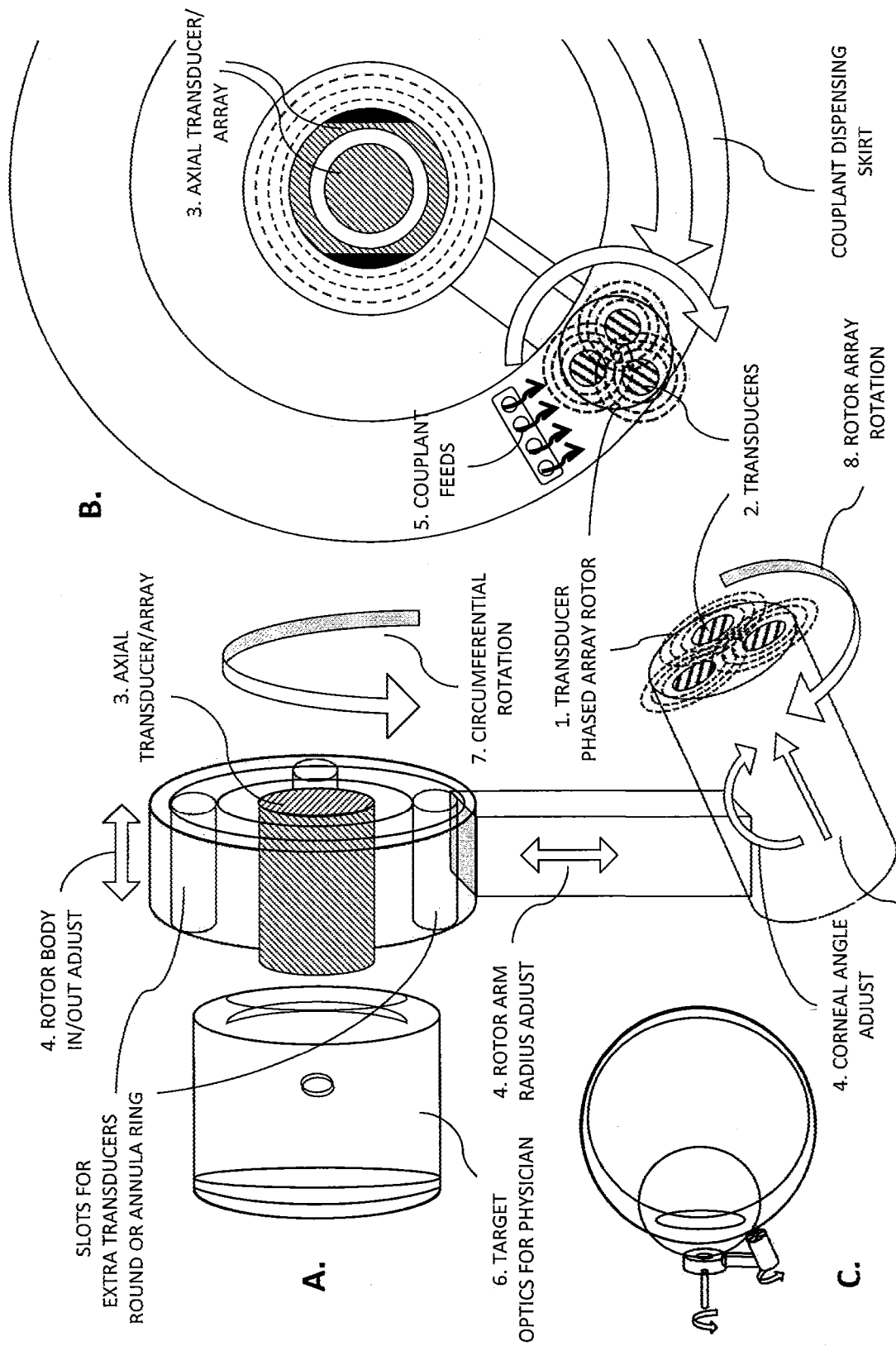
FIG. 12A-12C illustrate an embodiment of the phased transducer array rotor, in oblique side exploded view showing position adjustments and physician optics (A), rear view with an attached couplant skirt (B), and in schematic positioned at front of eye (C).

FIG. 12 illustrates an embodiment of the phased transducer array rotor, in oblique side exploded view showing position adjustments and physician optics (A), rear view with an attached couplant skirt (B), and in schematic positioned at front of eye (C). The transducer phased array rotor 1 in this embodiment has three transducers 2 that can rotate periodically or continuously, as desired. Couplant feeds 5 are part of a couplant dispensing skirt and the feeds automatically apply couplant gel to facilitate the transmission of sound energy from the transducers to the surface of the eye. An axial transducer/array 3 delivers sonic and ultrasonic frequencies axially to the corneal surface of the eye. A four-axis positioning mechanism 4 is shown (rotor body in/out adjust, rotor arm radius adjust, corneal angle adjust and rotor arm in/out adjust) that adjusts the rotor to the size and sphericity of the eye. The four-axis positioning adjustments are separate from the circumferential rotation 7 and rotor array rotation 8 of the device. Collimated target optics 6 allow the operator/physician to accurately align the transducers to the desired area of the surface of the eye. Slots in the rotor body for configuration of the axial transducer/array 3 with various types of transducers. Such a transducer array is built up out of transducers and fillers. An annular ring 'set' of transducers can be built up as pictured in FIG. 12B, or a single axial transducer as pictured in FIG. 12A, or the same with three satellite smaller transducers for a total of four. Such configurations may be useful in creating certain shapes of 'tsunami waves' for propagation through the anterior eye.

Figures 13A, 13B:
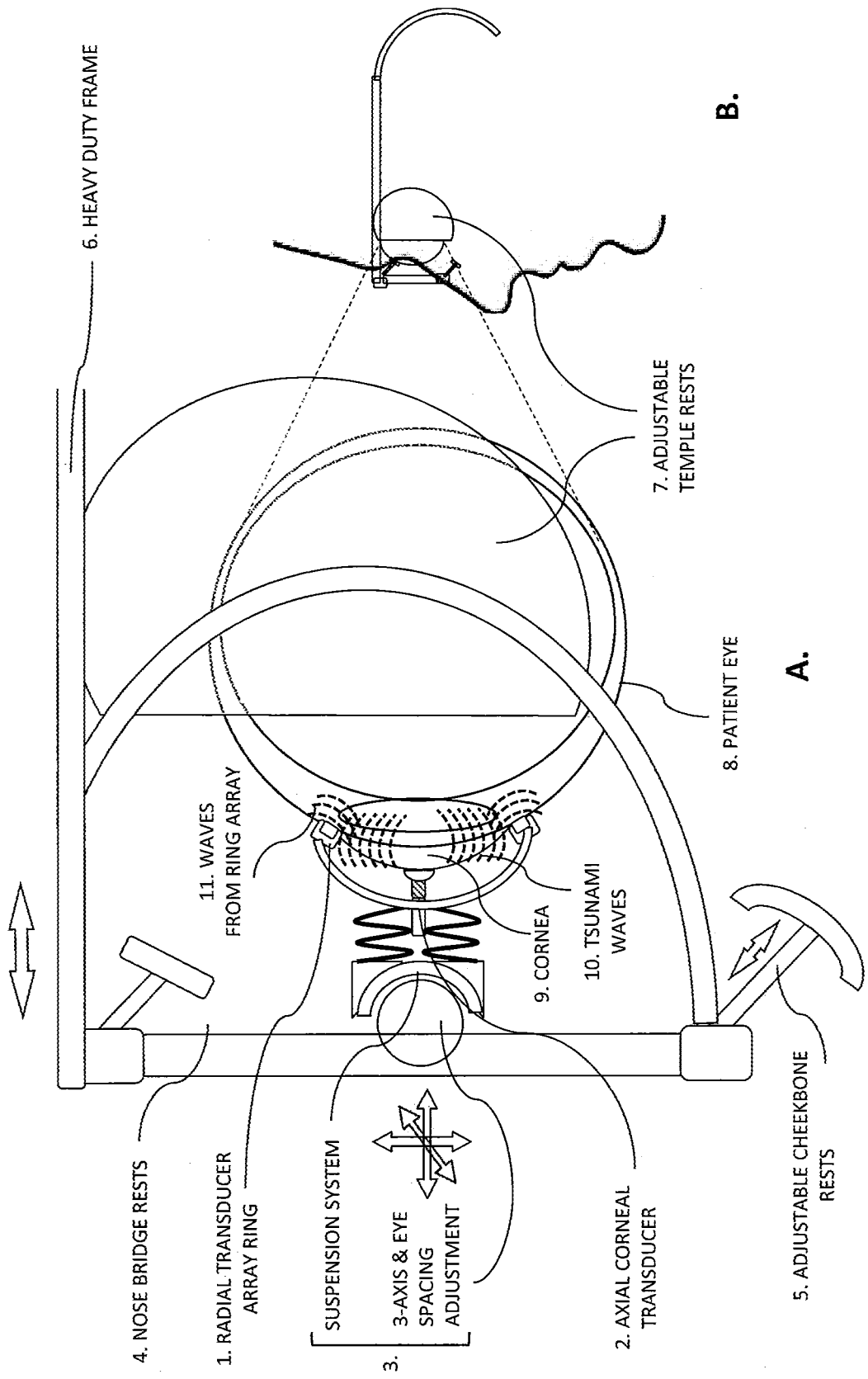
FIGS. 13A-13B shows an embodiment of glaucoma glasses in side view schematic with a radial transducer array ring with and topical axial transducer at the front of the cornea (A), and as the device sits on the patient head (B).

FIG. 13 illustrates an embodiment of an eyewear apparatus, in this case a pair of eyeglasses, in side view schematic with a radial transducer array ring with and topical axial transducer at the front of the cornea (FIG. 13A), and as the device sits on the patient head (FIG. 13B). The radial transducer array ring 1 has two or more transducers that deliver sound energy radially to the exterior surface of the patient eye 8. The axial corneal transducer 2 delivers sound energy axially to the cornea 9. Sound waves 11 are emitted from the ring array and tsunami waves 10 are created. Illustrative support elements of the device are shown including a heavy duty eyeglasses frame 6, adjustable temple rests 7, and nose bridge rests 4. A positioning mechanism 3 having a suspension system and 3-axis and eye spacing adjustment is also shown. The positioning mechanism positions the transducers on the surface of the eye and can be self-adjusting such that the position of the transducers is maintained when the eye moves.

Figure 14:
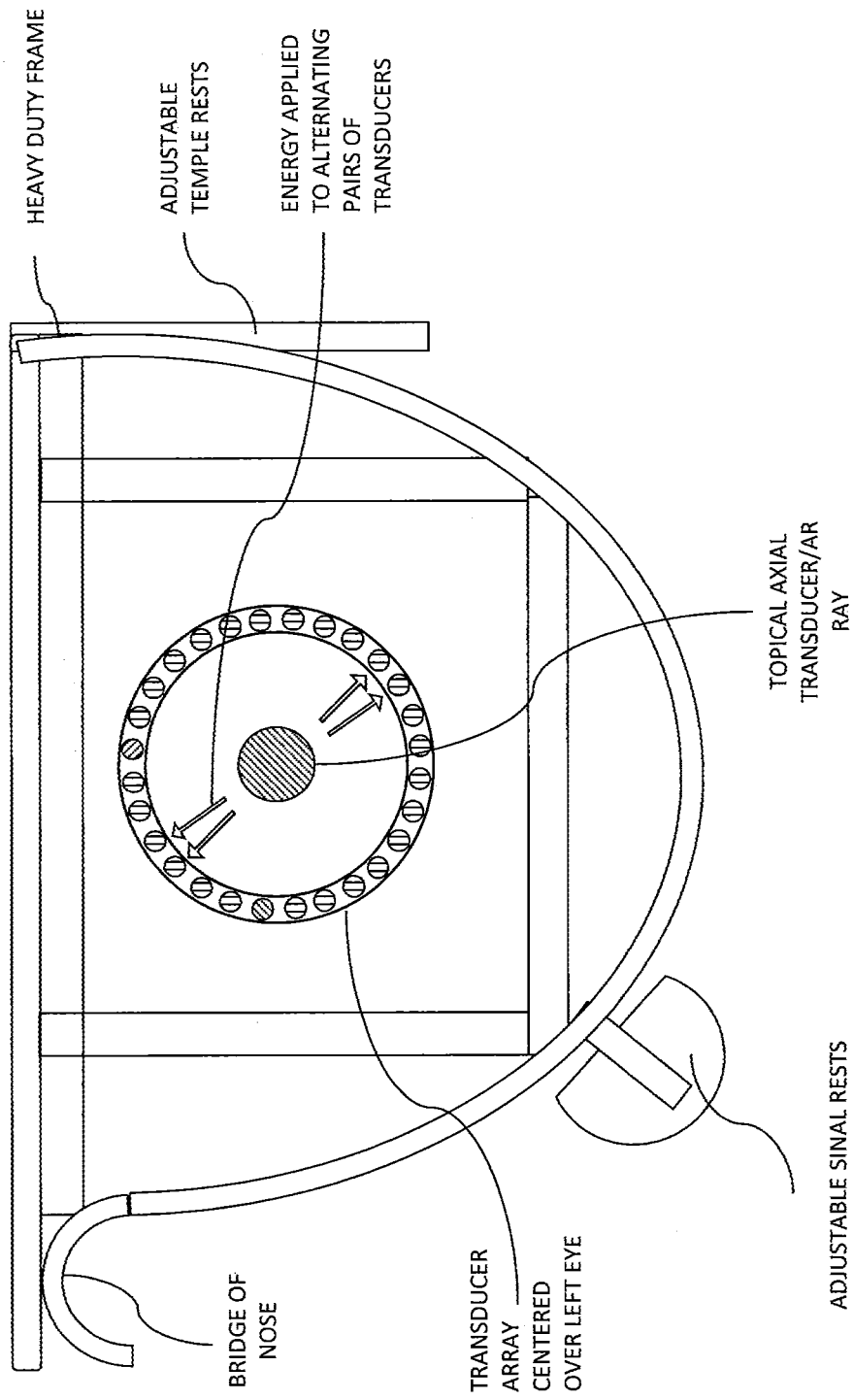
FIG. 14 shows a left-eye anterior schematic of an embodiment of the transducer array ring within the frame of the glaucoma glasses device.

FIG. 14 shows a left-eye anterior schematic of an embodiment of the transducer array ring within the frame of the glaucoma glasses device. The device shows one of its two topical corneal transducer arrays centered over the left eye with a topical axial transducer/array. Energy is applied to alternating pairs of transducers. The nose bridge rest, adjustable sinal nose rests, adjustable temple rests and heavy duty frame position the glasses over the eyes.

Figures 15A, 15B:
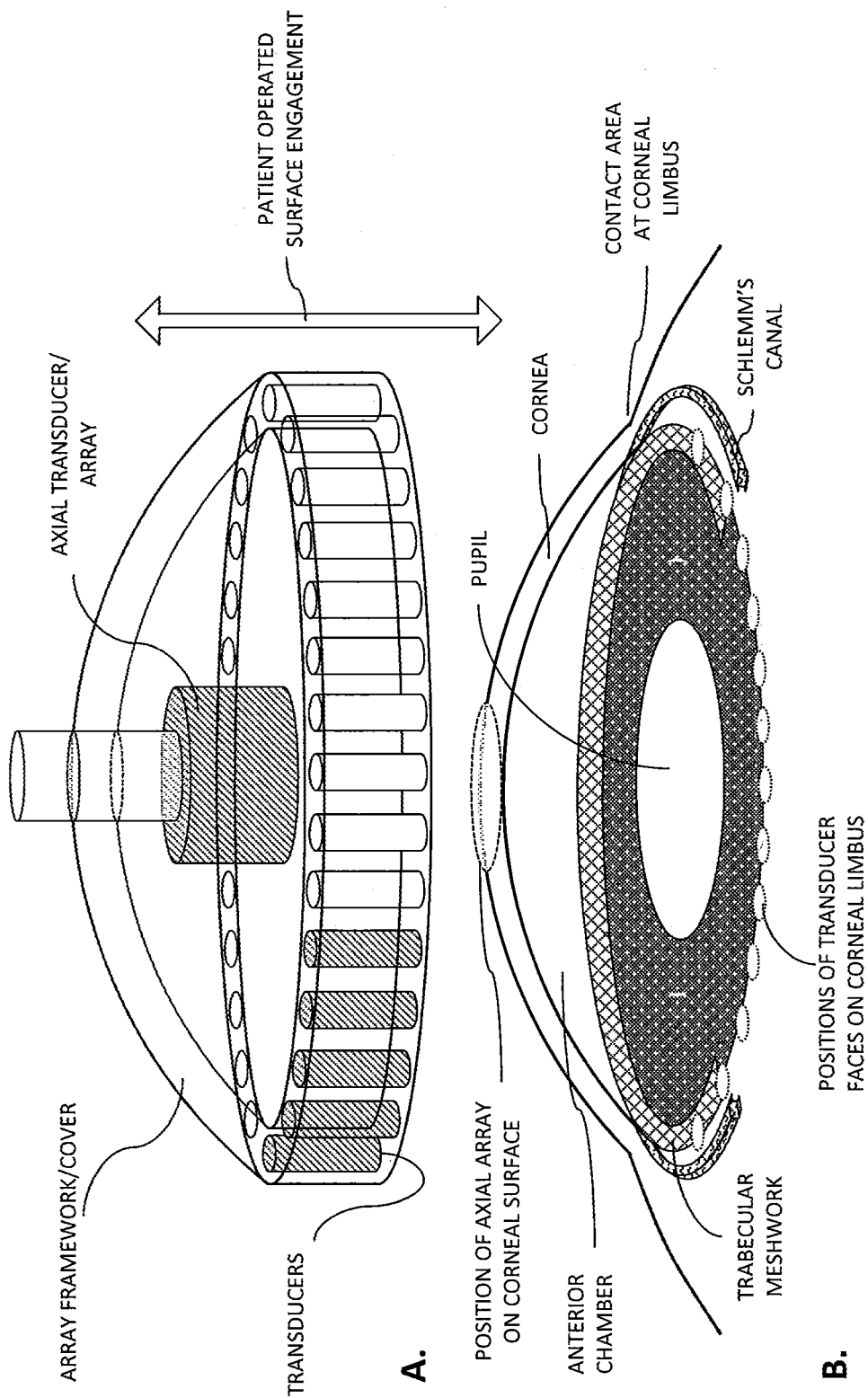
FIGS. 15A-15B illustrate a close-up oblique view of an exemplary glaucoma glasses transducer array (A), prior to being located against the surface of the patient eye (B), in oblique cutaway schematic.
Figure 16A:
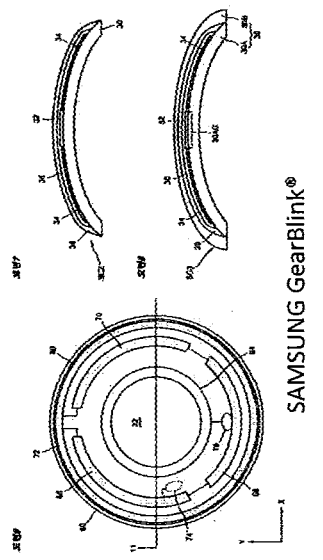
FIGS. 16A-16D show micro-electronic contact lenses known in the art. The SENSIMED Triggerfish® Sensor (SENSIMED/AG) (A) is a soft disposable silicone contact lens embedding a micro-sensor that captures spontaneous circumferential changes at the corneoscleral area. The Samsung Gear Blink™ (SAMSUNG INC.) Smart Contact Lens (B) has a display that can project images straight into the user's eye. The lenses are equipped with a built-in camera and sensors that can be controlled by blinking. Embedded antennas send content to a smartphone where the data is processed. Bionic contact lenses (C) are being developed to provide a virtual display that could have a variety of uses from assisting the visually impaired to the video game industry. The device will have the form of a conventional contact lens with added bionics technology in the form of augmented reality, with functional electronic circuits and infrared lights to create a virtual display. Novartis AG and Google Inc. are joining forces to work on a smart contact lens that monitors blood-sugar levels and corrects vision (D).
Figure 16B:
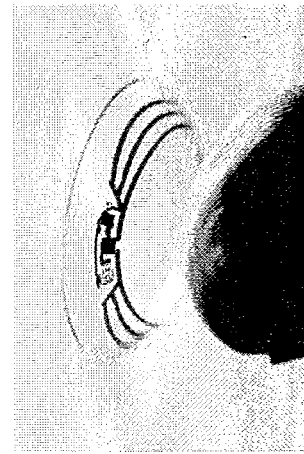
Figure 16C:
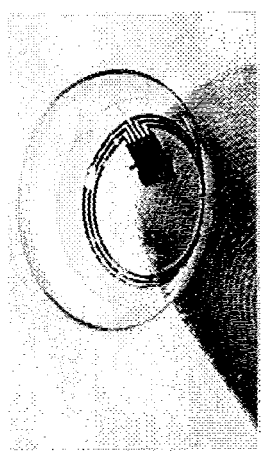
Figure 16D:
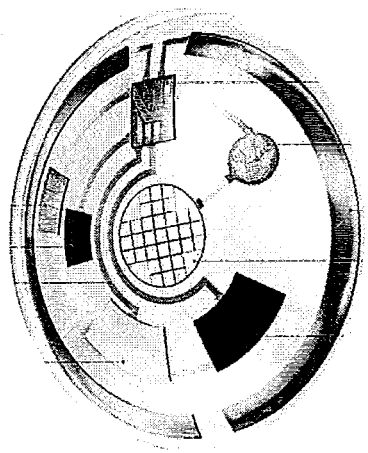

FIG. 15 illustrates an exemplary glaucoma glasses transducer array. FIG. 15A shows a close-up oblique view of an axial transducer/array with several transducers in the array ring covered by an array framework/cover. Patient operated surface engagement of the transducer array brings the array to the surface of the eye. FIG. 15B shows the position of the axial array prior to being located against the corneal surface of the patient eye, in oblique cutaway schematic. The transducer array contacts the eye at the corneal limbus and the positions of the transducer faces on the corneal limbus. The relative anatomy of the eye is shown (Schlemm's canal, TM, pupil and anterior chamber).

Figures 17A, 17B, 17C:
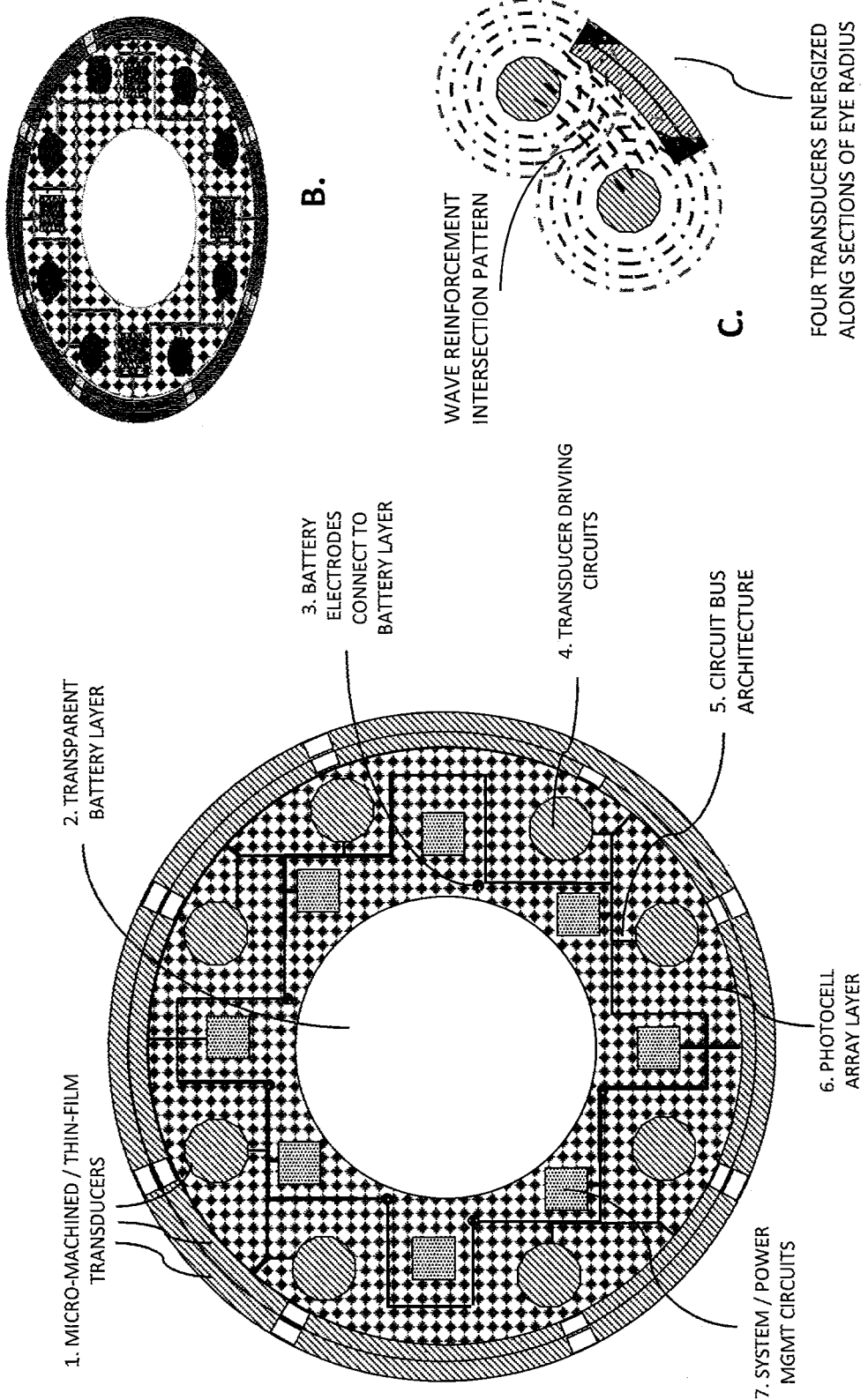
FIGS. 17A-17C show a rear view schematic of an embodiment of the transparent battery contact lens transducer array (A), a rear-view oblique appearance (B), and (C) a schematic of the resulting wave-pattern (C).

Contact lens technology has advanced far beyond correction of myopia (nearsightedness), hyperopia (farsightedness) and astigmatism, and now can be integrated with structures such as electronic circuits and used for numerous other applications (see FIGS. 16A-16D for examples of other uses of contact lenses). FIG. 17A illustrates a rear view schematic of an embodiment of a transparent battery contact lens transducer array with twenty-four transducers 1, for example, micro-machined or thin-film transducers, integrated into the contact lens. In this embodiment, eight transducers are circular, and sixteen transducers are on the periphery. As described herein, the size, shape and configuration of transducers in the transducer array can be varied according to the device or method being used. The transducers are operably linked to an integrated power source, here a layer containing a transparent battery 2 linked to the transducers by battery electrodes 3, transducer driving circuits 4, circuit bus architecture 5 and system/power management circuits 7. A photocell array layer 6 facilitates the capture of solar energy to power the transducers. FIG. 17B shows a rear view oblique appearance of the transparent battery contact lens transducer array. FIG. 17C shows a schematic of the resulting wave reinforcement intersection pattern formed by four transducers energized along sections of the eye radius.

Figure 18A:
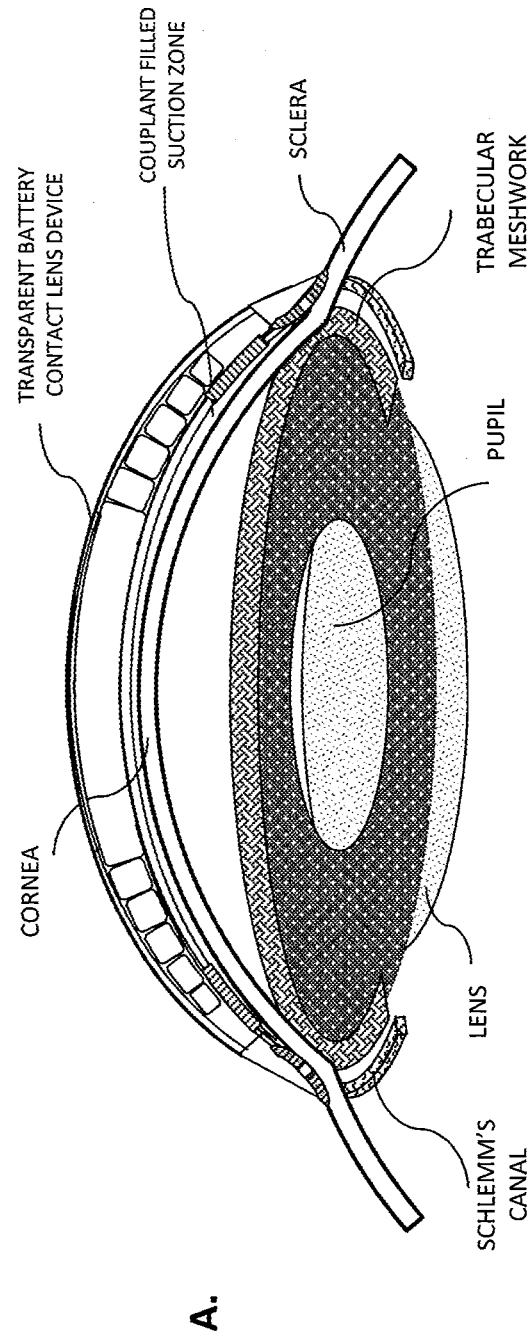
FIGS. 18A-18B show a sectional depiction of an embodiment of a transparent battery contact lens against the surface of the patient eye in oblique schematic (A), and the phased function of the transducer tension ring in promoting suction and positive grip to the patient eye while being energized (B).
Figure 18B:
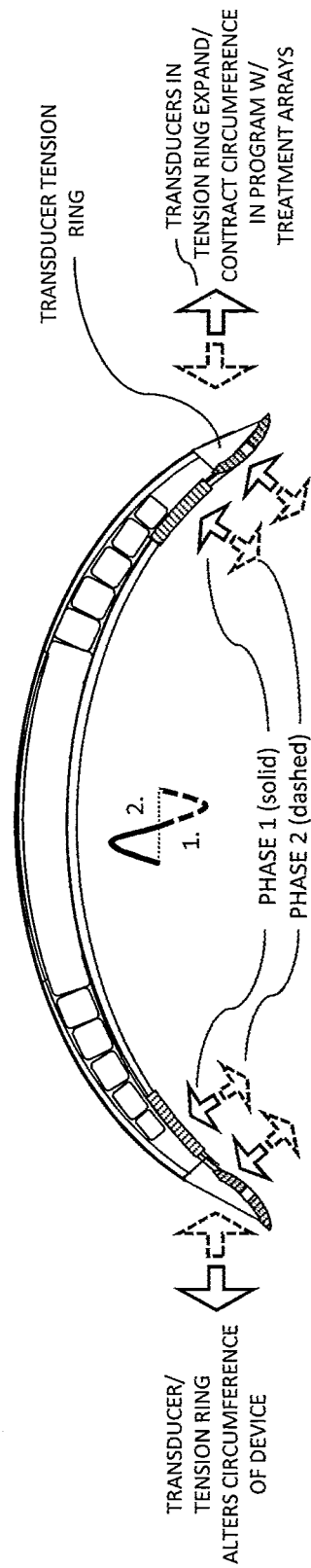

FIG. 18A shows a sectional depiction of an embodiment of a transparent battery contact lens against the surface of the patient eye in oblique schematic. The anatomy of the eye is shown (cornea, sclera, Schlemm's canal, TM, pupil and lens). At the interface of the transparent battery contact lens device is a couplant filled suction zone. FIG. 18B illustrates the phased function of the transducer tension ring in promoting suction and positive grip to the patient eye while being energized. A high frequency set of transducers at the periphery of a plastic contact lens will have difficulty staying in contact with the eye. Bubbles could develop and the device could fall off. The transducer tension ring is designed so that the entire circumference when energized by transducers within this ring, expands and contracts, in concert with the transducer array supplying treatment (Phase 1 and Phase 2). The net effect will be like a lamprey eel, sucking the surface of the eye. The programs of the tension ring and the treatment transducers will be phased to ensure the lens stays in place.

Figures 19A, 19B:
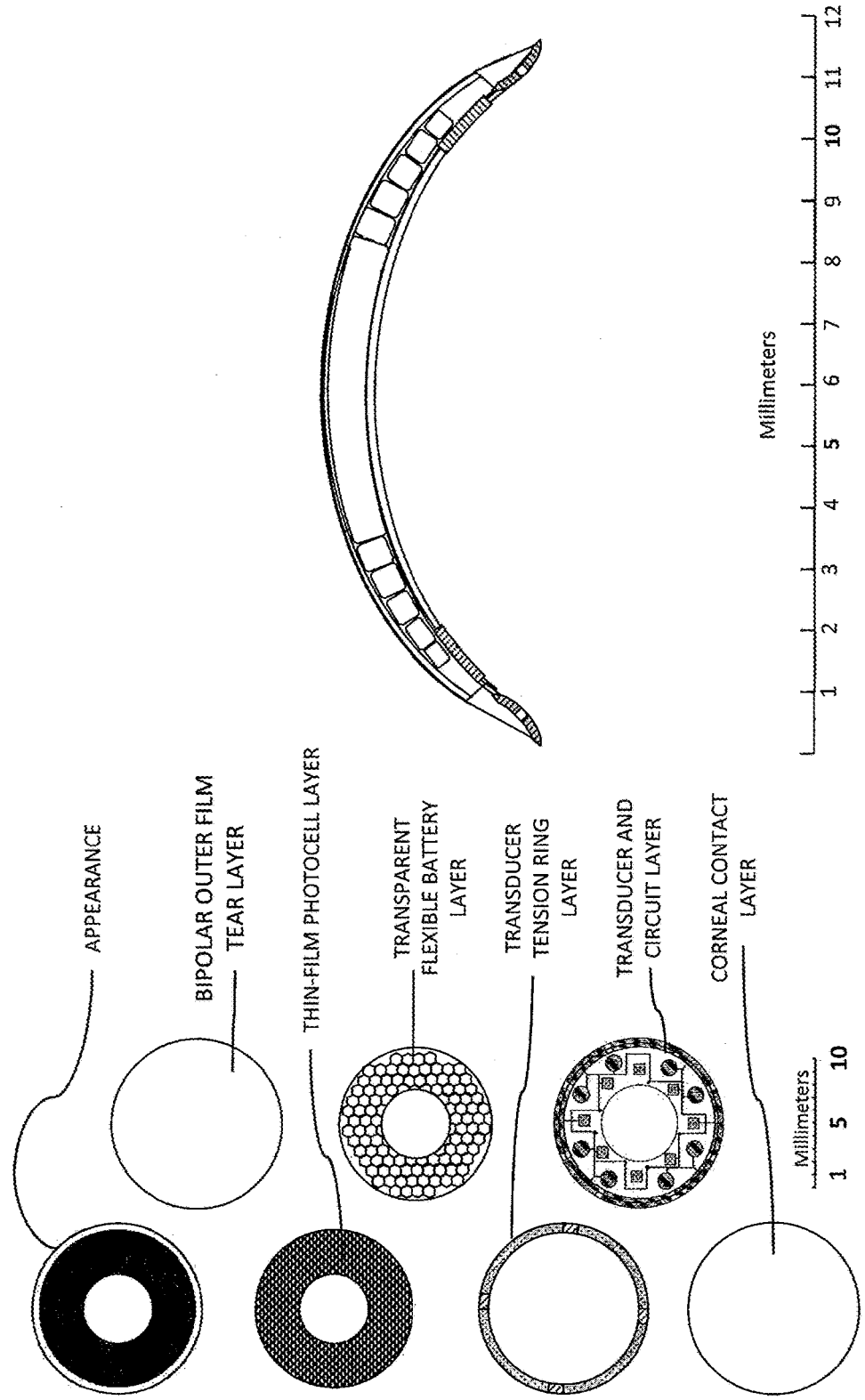
FIGS. 19A-19B illustrate an exploded rear view of each layer of an embodiment of a transparent battery glaucoma contact lens transducer (A), and a side view sectional schematic of the layers assembled (B).

FIG. 19A illustrates an exploded rear view of each layer of an embodiment of a transparent battery glaucoma contact lens transducer. The 'appearance' depiction combines the 'look' of the bi-polar outer film tear layer, and the thin film photocell layer beneath it. Some layers may be tinted to diminish the 'machine look' of a photocell. Some embodiments may have an additional UV layer that protects the eye from UV light (akin to sunglasses). The thin film photocell may be made of cadmium telluride (CdTe), copper indium gallium diselenide (CIGS), amorphous thin-film silicon (a-Si, TF-Si), or any other suitable material. In some embodiments, a photovoltaic cell may have a diameter of around 12 millimeters. The transparent flexible battery layer may contain any suitable transparent battery, for example, a transparent lithium ion battery or vanadium oxide graphene battery. The contact lens also contains a transducer tension ring layer (see also FIG. 18B). The transducer and integrated circuit layer may contain PZT thin film high frequency transducers (PMUTs), capacitive micro-machined ultrasonic transducers (CMUTs), or any other micro-machined or thin film transducer technology. The transducers may be round, annular ring, chordate shaped or other shapes designed to produce an overlapping effect, and convergent energies at the corneal limbus. The corneal contact layer interfaces with the surface of the eye. FIG. 19B is a side view sectional schematic of the layers assembled.

Figures 20A, 20B:
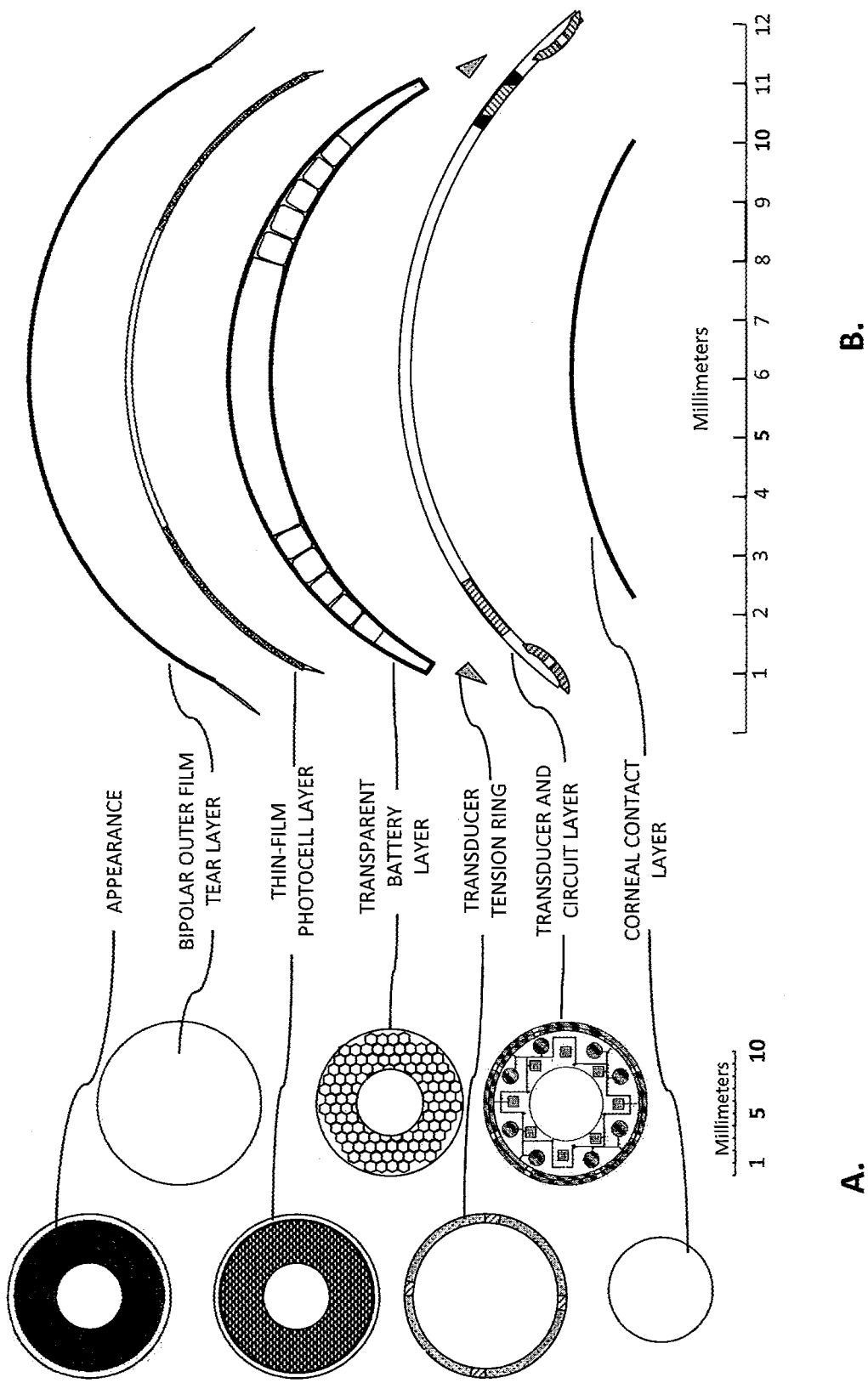
FIGS. 20A-20B show an embodiment of a transparent battery contact lens transducer array in exploded layer view from the rear (A), and sections of each layer from the side (B).

FIG. 20A shows an embodiment of a transparent battery contact lens transducer array in exploded layer view from the rear, and FIG. 20B shows the sections of each layer from the side. The contact lens layers are described in FIG. 19A.

Figures 21A, 21B:
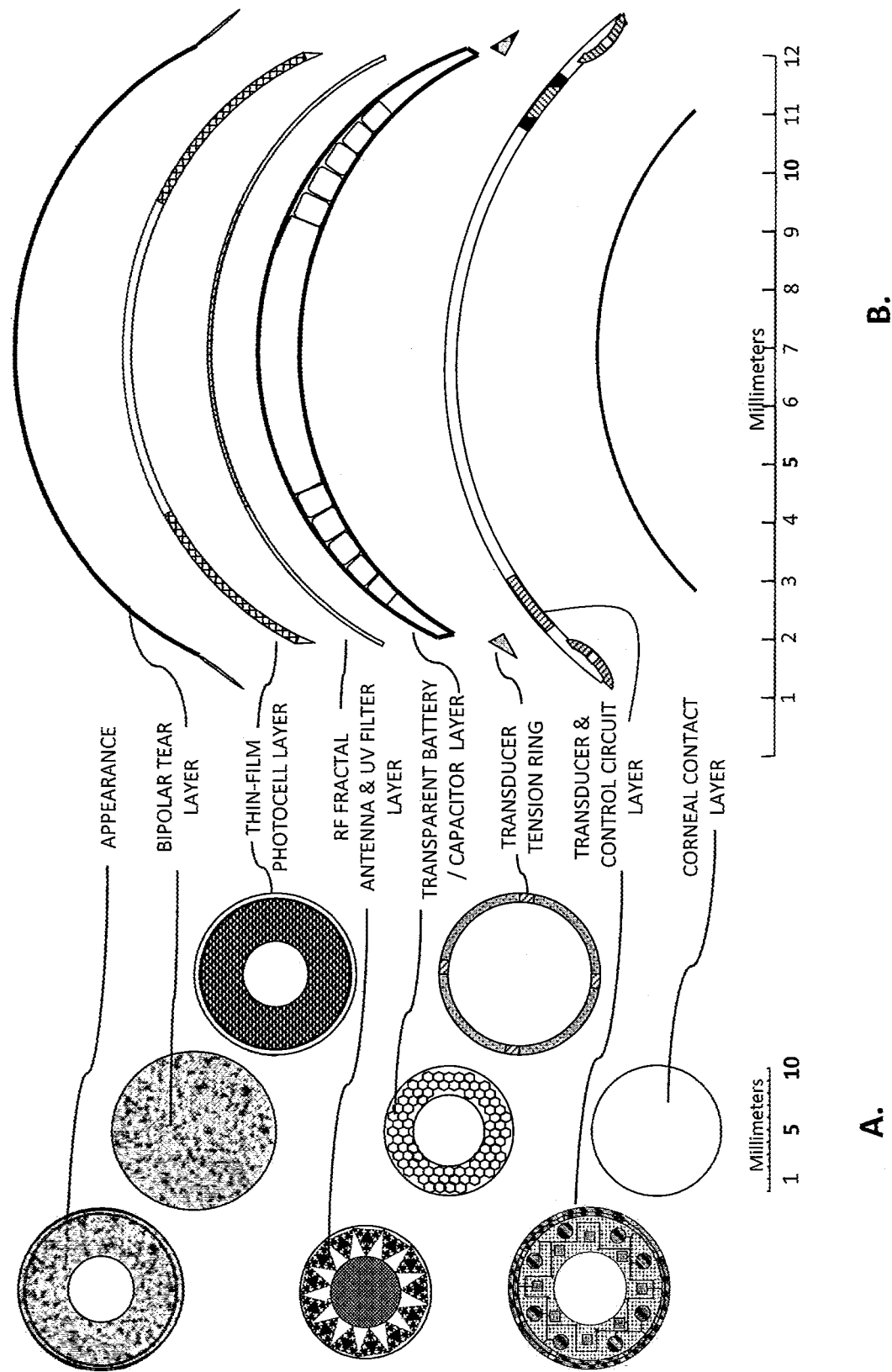
FIGS. 21A-21B show an exploded rear view of the layers of an embodiment of the wireless power transfer (WPT) contact lens transducer array (A) and exploded section side-view (B).

FIG. 21A shows an exploded rear view of the layers of an embodiment of the wireless power transfer (WPT) contact lens transducer array (A) and, FIG. 21B shows an exploded section side-view. Here the 'appearance' demonstrates the bi-polar tear layer has a certain opacity and tint designed to mask the appearance of the photocell layer. The other contact lens layers are as described in FIG. 19A. An additional layer is shown containing the RF fractal antenna and UV filter layer over the pupil.

Figure 22A:
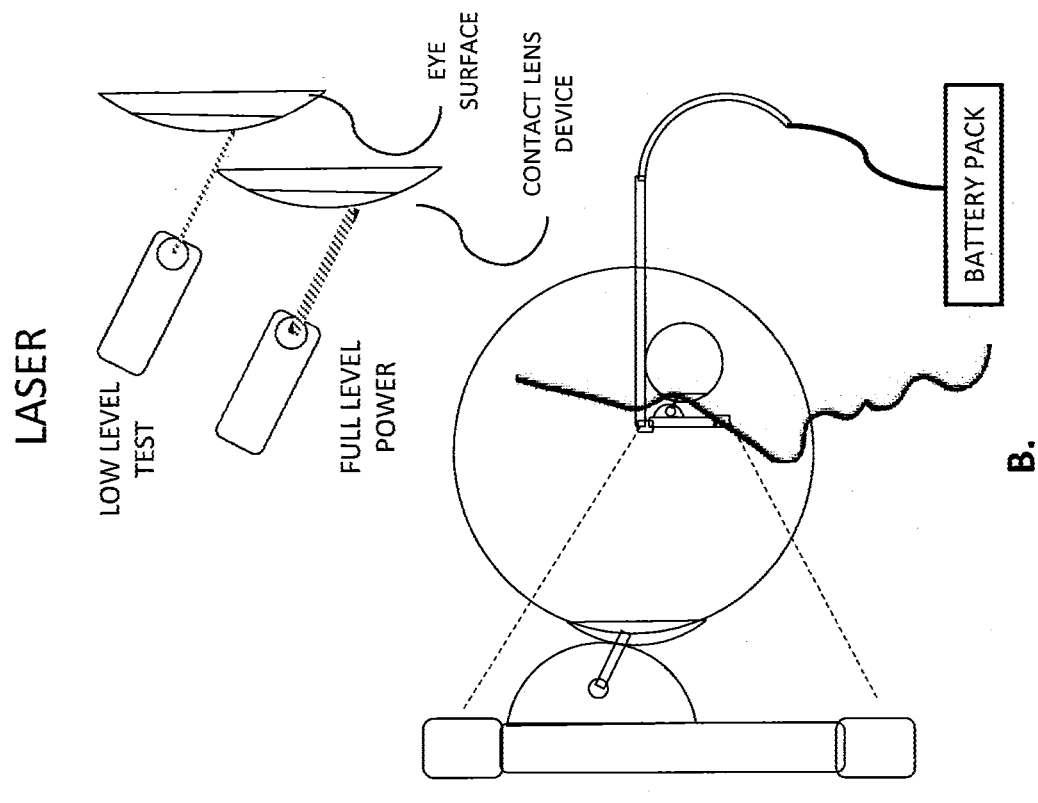
FIGS. 22A-22B illustrate two exemplary methods of powering the WPT contact lens, through electric induction (A) and by laser beam (B) using the wireless power transfer glasses device.
Figure 22B:
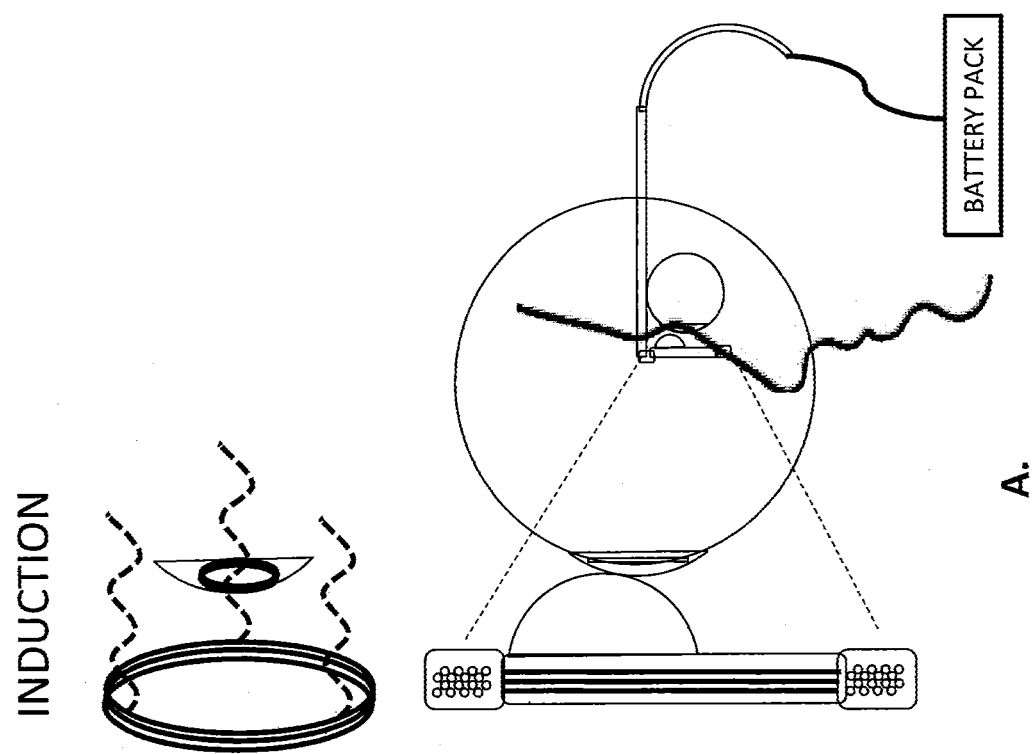

FIG. 22 illustrates two exemplary methods of powering the WPT contact lens, through electric induction (FIG. 22A) and by laser beam (FIG. 22B) using the wireless power transfer glasses device (see Example 4). In another example, energy is transferred from a coil in the eyeglasses to a coil in the contact lens by magnetic induction. In another example, energy is transferred from a laser beam in the eyeglass frame to a photocell in a contact lens where an RF or IR feedback circuit inside the contact lens calls for power. Safety shutoff control circuitry can be included. Low level laser burst 'tests' the position of the eye. A higher power laser beam fires charging bursts but is interrupted immediately if full power is not received by the contact lens.

Figures 23A, 23B, 23C, 23D, 23E, 23F:
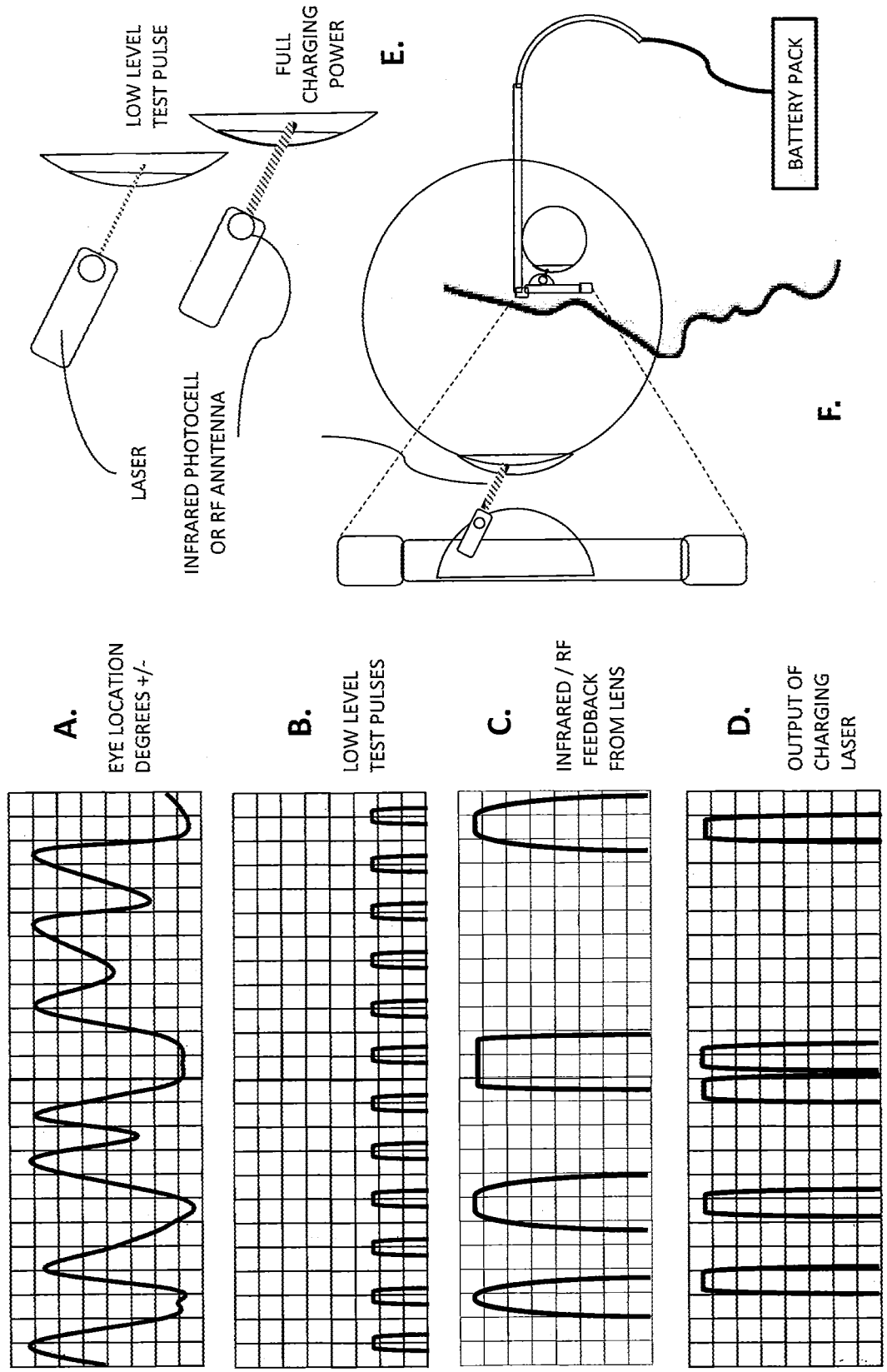
FIGS. 23A-23F illustrate a sequence by which an embodiment of the laser WPT glasses transfers power to the transparent battery contact lens device: depending upon the location of the eye (A) the contact lens either confirms a 'safe' response based a test pulse from the laser (B), the lens confirms with immediate feedback (C) or not, and if so, output (D) is made at a time when safe to the eye. Panel (E) illustrates in schematic test and full levels of the laser as well as the RF or infrared feedback system. Panel (F) depicts the relative size and complexity of the charging glasses, with a battery pack worn on the person of the patient.

FIG. 23 illustrates a sequence by which an embodiment of the laser WPT glasses transfers power to the transparent battery contact lens device that uses a laser beam to wirelessly transfer power to a contact lens. Depending on the location of the eye (FIG. 23A), the contact lens either confirms a 'safe' response based a test pulse from the low level laser (FIG. 23B), the lens confirms with immediate feedback via IR/RF signal from the lens (FIG. 23C) or not, and if so, output of the charging laser (FIG. 23D) is made at a time when safe to the eye. If the feedback signal ends or indicates movement of the eye, charging terminates. FIG. 23E illustrates in schematic the low level test and full charging levels of the laser as well as the RF or infrared feedback system. FIG. 23F depicts the relative size and complexity of the charging glasses, with a battery pack worn on the person of the patient.

Figure 24:
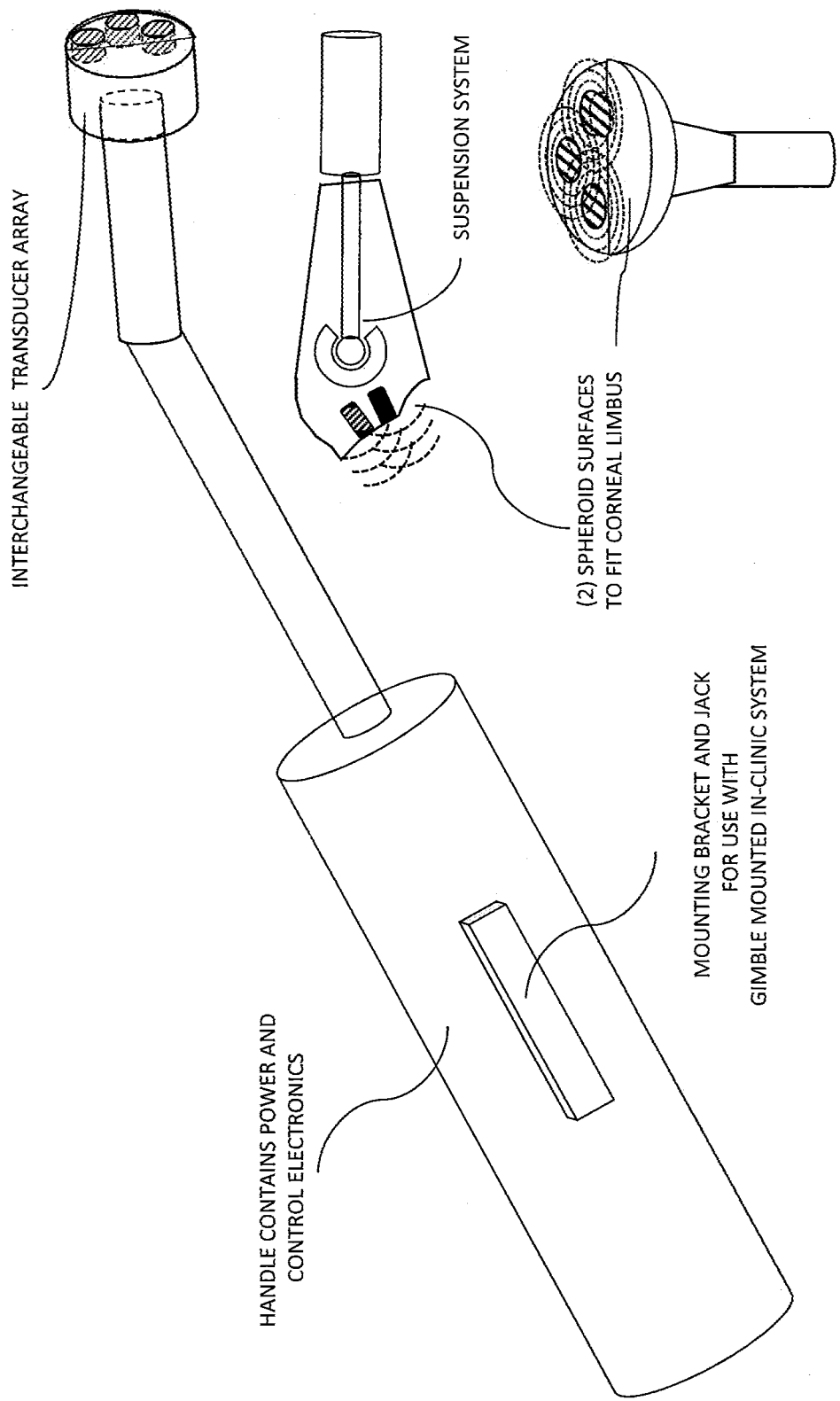
FIG. 24 illustrates an embodiment of the handheld transducer array unit with three transducer array attachments and cutaway of a suspension system.

FIG. 24 illustrates an embodiment of the handheld transducer array unit with three transducer array attachments and cutaway of a suspension system (see Example 6). The handle of the device contains power and control electronics. A mounting bracket and jack can be included for use with the gimbal-mounted in-clinic system (see Example 1). A suspension system and two spheroid surfaces can be used to adjust the phased transducer arrays.

Figure 25:
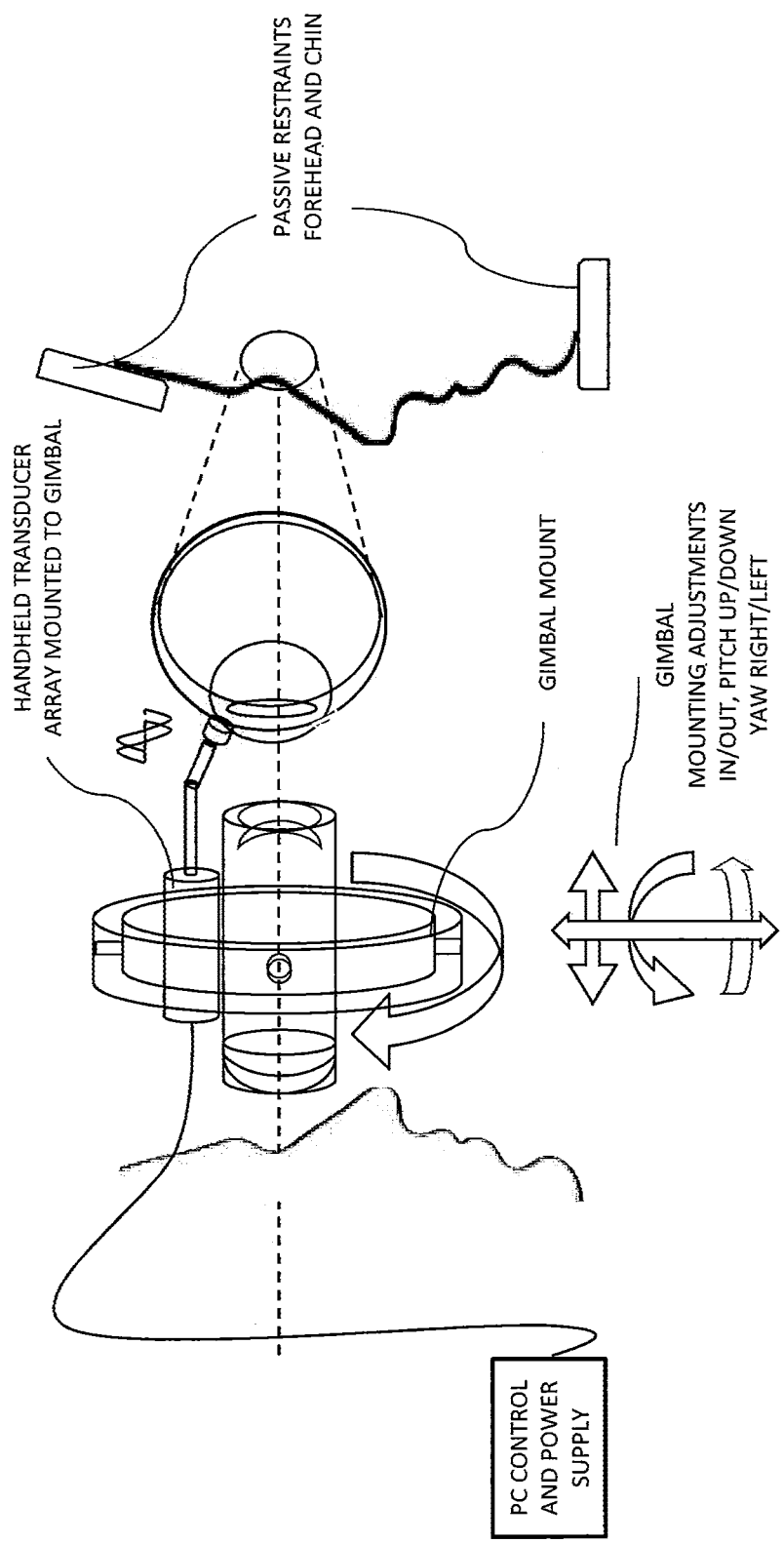
FIG. 25 depicts an embodiment of the handheld transducer array attached to the lower cost gimbal mounting device to deliver more precise programs of treatment than with the same system handheld.

FIG. 25 depicts an embodiment of the handheld transducer array attached to the lower cost gimbal mounting device to deliver more precise programs of treatment than with the same system handheld. This device can be used to verify the treatability of a patient with frequency therapy. It provides a quick application of sound energy to test a treatment program. It can be used to set up repeatable programs for use on other devices. The suspension applies power only when positively registered against the eye. This device may be adapted for topical axial stimulation. The gimbal unit shown here is an attachment for the Handheld Transducer Array (Example 6) and is not necessarily the same as the In-Clinic Device (Example 1).

Figures 26A, 26B, 26C:
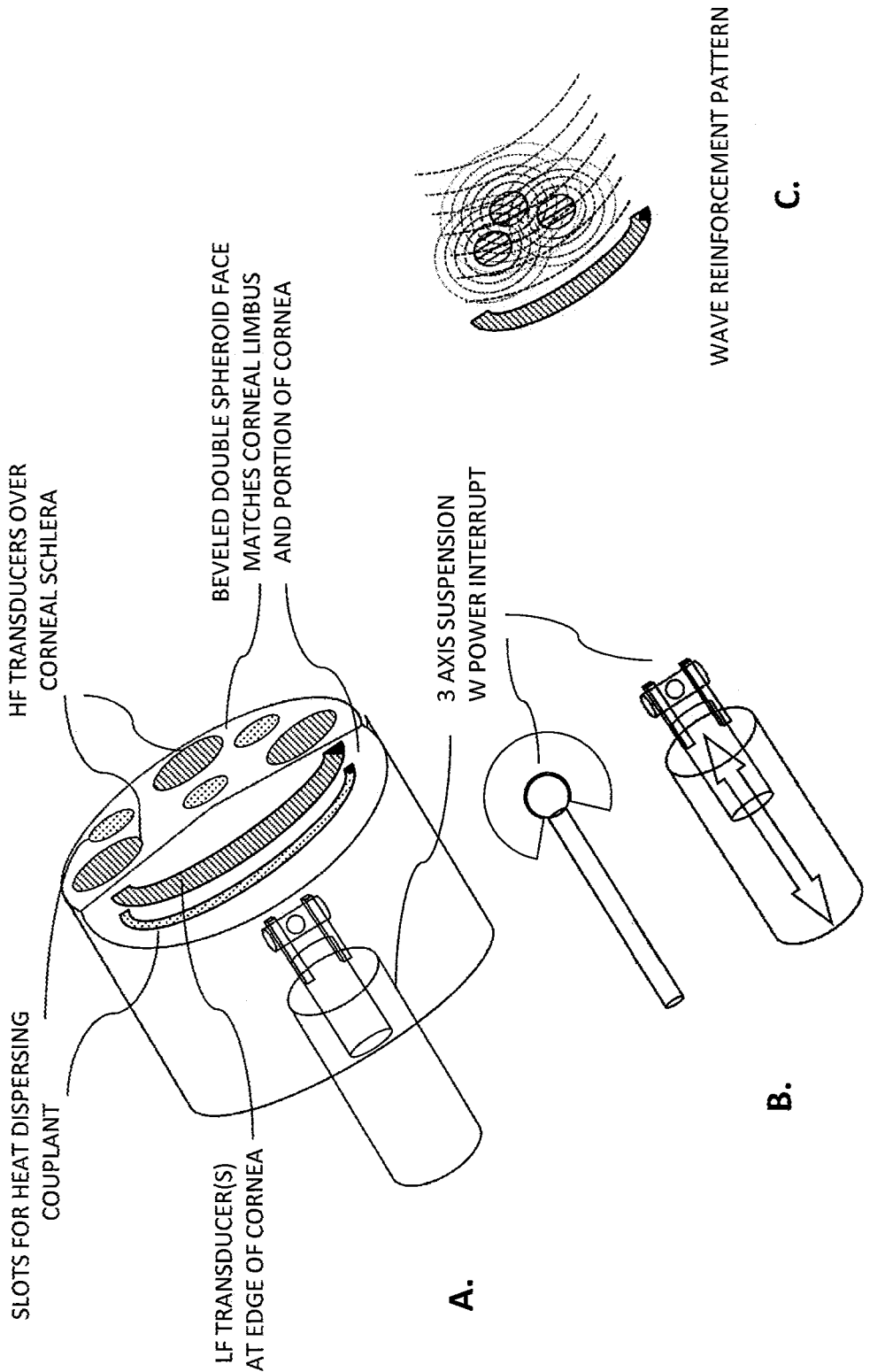
FIGS. 26A-26C depict close-ups of an embodiment of an array attachment for the handheld transducer array (A), two forms of suspension (B), and wave intersections resulting from such a configuration (C).

FIG. 26 shows a transducer array with spheroid surfaces fitted to the corneal limbus with three-axis suspension. FIG. 26A shows an embodiment of an array attachment for the handheld transducer array, with LF transducers at the edge of the cornea and HF transducers over the corneal sclera. The beveled double spheroid face matches the corneal limbus and a portion of the cornea. There are slots for heat dispersing couplant. FIG. 26B shows a close-up of two examples of three-axis suspension with power interrupt. FIG. 26C shows wave intersections resulting from such a configuration.

Figures 27A, 27B:
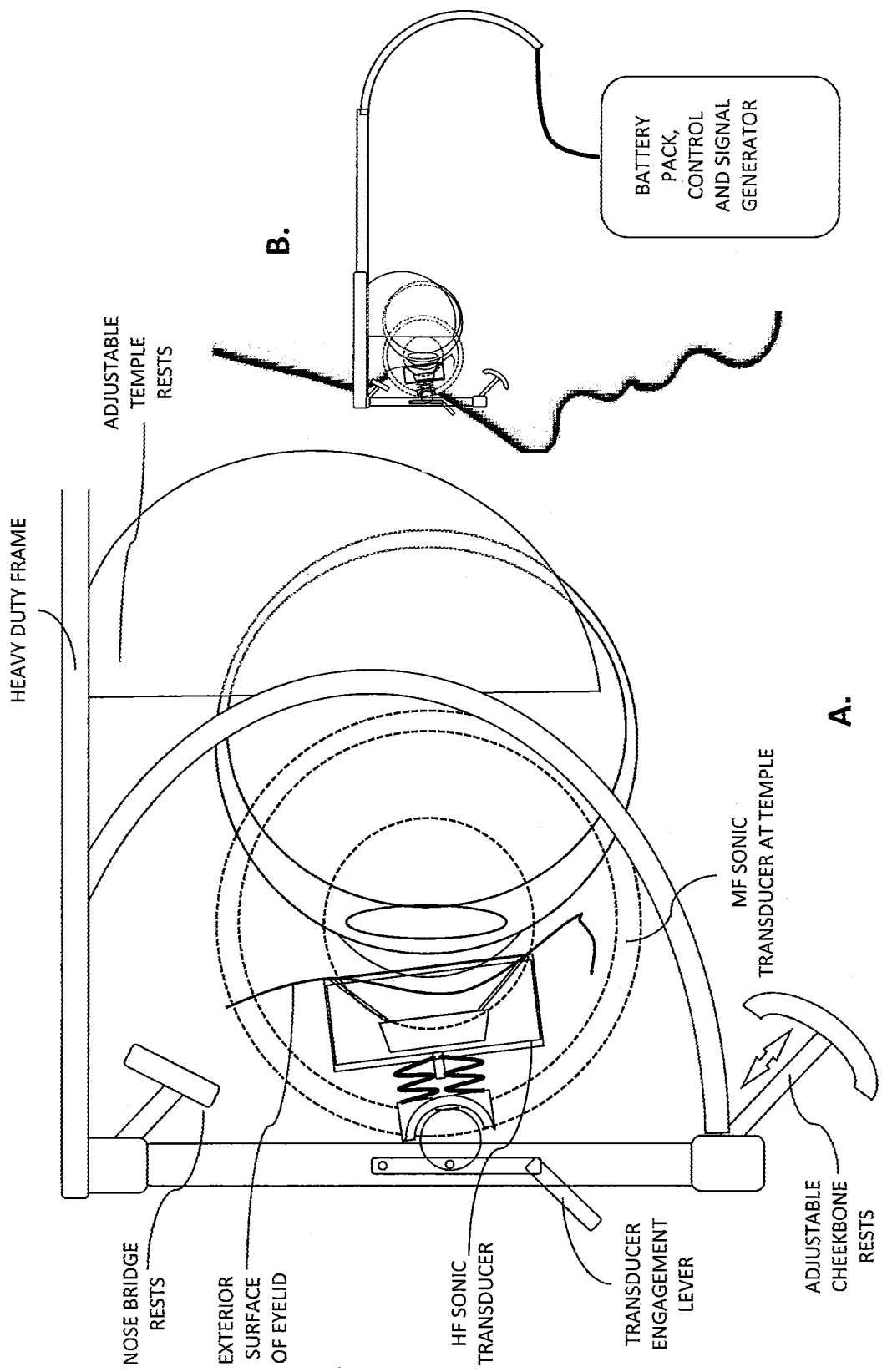
FIGS. 27A-27B depict an embodiment of the sonic frequency glaucoma glasses in side-view schematic with the location and suspension of a HF Sonic Transducer against the eyelid (A), and as the device appears installed on patient head (B).

FIG. 27 depicts an embodiment of the sonic frequency glaucoma glasses (see Example 7). FIG. 27A shows a side-view schematic with the location and suspension of a HF Sonic Transducer against the exterior surface of the eyelid, an MF Sonic transducer at the temple and a transducer engagement lever. The device is supported and positioned by a heavy duty frame, adjustable temple rests, adjustable cheekbone rests and nose bridge rests that sit atop the patient's nose. FIG. 27B shows the device as it would appear installed on patient head with the battery pack, control and signal generator operably linked to the glasses.

Figure 28:
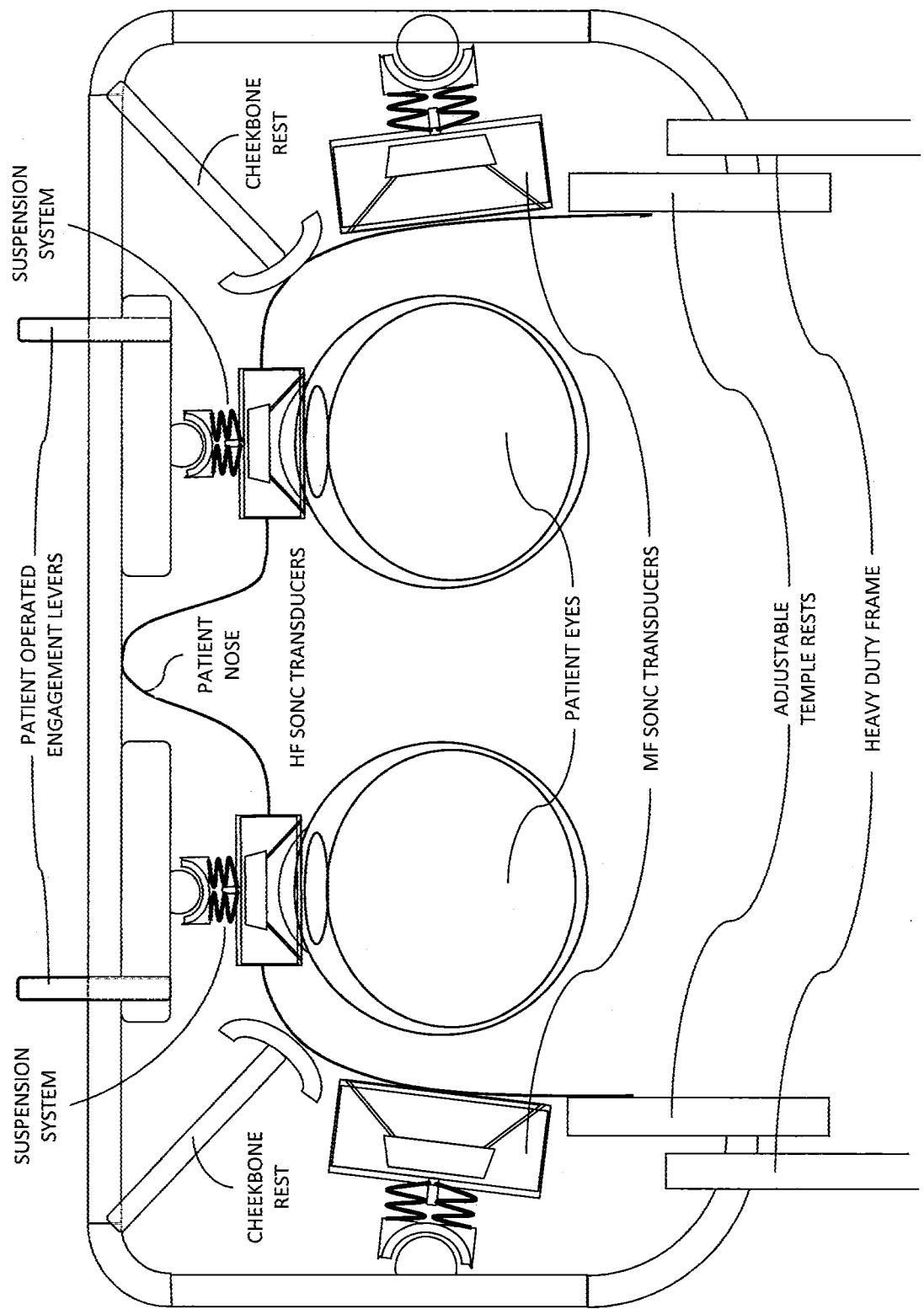
FIG. 28 depicts a top-view schematic of an embodiment of the sonic frequency glaucoma glasses.

FIG. 28 depicts a top-view schematic of an embodiment of the sonic frequency glaucoma glasses. The device is supported and positioned by a heavy duty frame, adjustable temple rests, adjustable cheekbone rests and nose bridge rests. HF Sonic transducers and MF Sonic transducers are adjusted and positioned at the patient's eyes using a suspension system. The patient controls engagement of the transducers using patient-operated engagement levers.

The Eye and Sound Energy

Eye Anatomy favorable to Sonic and Ultrasonic Treatment.

The anatomy of the human eye and its drainage system are favorable to a frequency-based therapeutic approach to glaucoma. The Schlemm's canal and TM are 0.5 millimeters below the surface of the corneal limbus, the border of the cornea and the sclera, or white portion of the eye. The TM is a three-layered meshwork is designed to slow flow of the intraocular fluid out of the eye. The fluid in the Schlemm's canal is directly adjacent to the finest meshes of the TM. The outermost layers of the TM borders on the Schlemm's canal and account for the most resistance to aqueous fluid outflow. Clogged layers of the TM raise the resistance and increase intraocular pressure in many forms of glaucoma. This geography indicates that the fouled regions of the TM are within acoustic stimulation distance of the fluid in the Schlemm's canal.

In some embodiments of the devices disclosed herein, the introduction of sonic and/or ultrasonic energy at an exterior surface of the eye, such as in the region of the corneal limbus or at the cornea itself, near the corneal limbus, or at the front of the cornea itself.

Sound Energy and Health.

In Ancient India sonotherapy has been used to treat all forms of disease. In general it is known that low frequencies promote health. All forms of exercise are repeated rhythmic stresses placed on different parts of the body, from the use of a trampoline (0.5 Hz) to walking (1 Hz). Adult heartbeats (0.8-2.0 Hz) are known to soothe and relax small children. Drum beats (1-30 Hz) and singing (80-260 Hz) have demonstrable health effects on respiration and circulation while low frequencies relax muscles and tendons. Higher sonic and low ultrasonic frequencies encourage biological processes, by moving waste and breaking up debris. Low frequency ultrasound accelerates healing of bone fractures and encourages the circulation of lymph and blood.

Sound and Ultrasound

For the purposes of this disclosure, "sonic frequency," as used herein, means any frequency within the range of from about 16 hertz to about 20 kilohertz. For the purposes of this disclosure, "high sonic frequency," as used herein, means any frequency within the range of from about 5 kilohertz to about 20 kilohertz. For the purposes of this disclosure, "ultrasonic frequency," as used herein, means any frequency within the range of from about 20 kilohertz to about 3 gigahertz. For the purposes of this disclosure, "low ultrasonic frequency", as used herein, means any frequency within the range of from about 20 kilohertz to about 200 kilohertz. For the purposes of this disclosure, "high ultrasonic frequency," as used herein, means any frequency above 200 kilohertz.

Ultrasound.

Ultrasound is like all sonic energy except that it occurs at frequencies that are inaudible to human beings. The distinction between infrasonic, sonic, and ultrasonic sound is based only on audible range. This is a species-dependent distinction. Dolphins and bats for instance, navigate with and locate prey using frequencies that are perfectly audible to themselves, but inaudible to human beings because they are too high in pitch.

Use in Medicine and Industry.

Audible tones play a key role in the healing of injured nerves and broken bones. Ultrasound speeds the healing of bone, although it is not known why this occurs. Medical ultrasonography is currently used in all parts of the body. Cavitation ultrasonics plays an important role for the destruction of kidney stones in shock wave lithotripsy, as well as with phacoemulsification of cataracts of the eye.

Intra-operative and laparoscopic ultrasound are used to cut and ablate diseased tissue. Focused ultrasound surgery (FUS) or high intensity focused ultrasound (HIFU) are also gaining traction across the world, mainly in Europe, India and Canada, to treat such brain lesions, uterine fibroids and prostate cancers.

Numerous other uses for ultrasound are known in the art, for example, imaging systems, inspection of critical components and quality control. The mining and materials industry uses sonic and ultrasonic energies to vibrate, sort and blend materials of all kinds, liquids and solids alike. Sonic energy is used in construction site to compact and mold concrete. The food industry uses ultrasound to mix and emulsify foodstuffs such as mayonnaise and margarine. Vibration is used to move heavy pieces of equipment over flat surfaces.

Physical Consequences of Vibration

Undulation.

Any soft fluid filled body, such as living tissue, is altered physically and dimensionally when affected by sonic or ultrasonic vibration. Undulation is the process of physical 'massage' of the affected body when low frequency sonic vibration occurs. This process is similar to a rug being shaken, to dislodge the dirt within its fibers. Undulation of the trabecular meshwork (for example, by burst, pulse or impact), may play an important role in dislodging debris and allowing fluid to flow past the progressively tighter meshes to the Schlemm's canal.

Wavelength and amplitude are inversely proportional for a sound wave carrying the same energy. Therefore when working with soft tissues like the eye it is unlikely that anything but low energy waves will be used in the sonic range, whereas total energies may rise safely as frequency increases. The devices and methods disclosed herein utilize the character of both high and low frequencies, to directly address the problems of clearing TM blockage, and expediting the flow of intraocular fluid.

Liquefaction.

Liquefaction (from geology: 'soil liquefaction') is a process by which mixtures of solid particles behave like liquids when agitated. Large buildings will sink into the earth when the ground is shaken enough, and empty hollow voids such as concrete sewers or drainpipes may actually rise to the surface of the ground after a seismic event. In industry, when certain frequencies are applied to sieves and filters of almost any dimension, solid materials of the requisite size pass through easily. Most importantly liquids pass through the most easily, and the passing of intraocular fluid out of the anterior eye is the primary objective in treating glaucoma. While the debris clogging the TM of glaucoma patients is far from behaving like perfect solid mixtures of aggregates such as sand or gravel, this debris will have some solid constituents and some principles of liquefaction may be applicable.

Cavitation.

Cavitation is the formation of bubbles resulting from a phase change from liquid to gas, and back again to a liquid, and can be elicited by any sonic or ultrasonic frequency. Dolphins can swim so fast that large and painful cavitation bubbles occur at the edges of their flippers. This keeps them from using their highest speeds except when absolutely necessary. Tuna are able to swim at speeds that regularly cavitate seawater around their fins which are bony and have almost no nerve endings. Cavitation bubbles are major sources of noise and inefficiency around boat and submarine propellers, facts of physics that costs the marine industry hundreds of millions of dollars per year.

Cavitation occurs in the xylem of vascular plants when the pressure of sap within the xylem falls so low that liquid water vaporizes locally. Cavitation causes coastal erosion when vapor pockets of incoming waves are forced into cracks in the rocks. When the force of the waves compresses the vapor pockets the bubble implodes, becoming liquid, giving off energy that blasts the rock apart.

Currently, sonoporation is being tested to see whether cavitation may be used to transfer large molecules into biological cells. Cavitation plays a role in the destruction of kidney stones in shock wave lithotripsy. Nitrogen cavitation is used in research to lyse cell membranes while leaving organelles intact. Cavitation plays a role in non-thermal, non-invasive fractionation of tissue for treatment of a variety of diseases, and may play a role in high frequency focused ultrasound, a thermal non-invasive focused treatment methodology for prostate cancer and blood clots. Ultrasound can be used to encourage bone formation in post-surgical treatments.

Cavitation is the force behind ultrasonic cleaning in many industries today and is one of the physical consequences of vibration contemplated by the devices and methods disclosed herein, for example, cavitating liquid in the Schlemm's canal, within the TM, and also the anterior chamber to break apart debris clogging the TM.

While cavitation is possible at any frequency, the use of sound and ultrasound at sea level pressures in stationary fluids or within living tissues, generally requires the use of ultrasonic frequencies. Whether cavitation occurs or not depends on a number of factors, including an increase in the amplitude of the sonic or ultrasonic wave, a decrease in local ambient fluid pressure, an increase in the frequency of the sonic or ultrasonic wave, and the viscosity and makeup of the fluids stimulated by transducer energy.

Thixotropy.

The make-up of debris clogging the TM of a glaucoma patient may vary depending on the type of the disease. It is believed that the majority of TM debris consists of a mixture of melanin granules and un-decomposed melanocytes or uveal cells as well as potentially other cell types and material from within the anatomy of the eye. It is therefore important to consider the physical properties of debris clogging the TM. This debris can be considered to be thixotropic, i.e., it demonstrates non-Newtonian properties when subjected to a shear force such as acoustic energy, for example fluids, gels and mixtures that are viscous under static conditions but become less viscous when shaken, agitated or stressed (time-dependent viscosity).

Thixotropic mixtures respond to a threshold of shear stress by a change (lowering) of viscosity. A unique non-Newtonian property of thixotropic fluids is that this viscosity change occurs within a specified radius of the locus of shear energies. The fluids demonstrate an either/or behavior, that can be utilized to confine the action of applied acoustic stimulation. That is they suddenly experience a thixotropic decrease in viscosity due to applied shear forces, a change which occurs suddenly and completely wherever those shear forces are in excess of a particular threshold, and within a specific radius of the source of the shear force, such as a transducer or transducer array. Ketchup is probably the best known thixotropic mixture that responds to frequency, i.e. agitation, in order to be induced to flow more quickly.

If the debris in the TM is a thixotropic mixture of partly decomposed melanocytes, melanin granules, uveal cells, etc. then when the correct shear force is reached, the coagulated debris will behave like a liquid. The action will occur within a definite radius of the energy source (Effective Area≤$r_n$ for Energy I=P/4π$r_n^2$) and the action occurs evenly within precise radius of energy source if debris rheology is consistent. The action will continue as long as shear energies are applied and for some time afterwards as well. Shear forces need not be applied with ultrasonic or cavitation frequencies, cavitation or sub-cavitation frequencies may alter the thixotropic properties of the debris, and reduce energies needed to produce lower viscosities and hence lowering IOP. Thixotropic fluids will be the best absorbers of cavitation energy, as their composite solids are fragmented further into finer dimensions. The all or nothing behavior of thixotropic fluids allows for a targeted approach. The radius of action of a shear stress from acoustic energy allows for a designed radius of action around a transducer array.

Ablation.

Sonic energy can also be used to ablate, or destroy, living tissue. Diseased tissues ablation refers to the use of focused ultrasound surgery (FUS) or high intensity focused ultrasound (HIFU) to destroy cancers, brain lesions, uterine fibroids and prostate cancers. In most of these treatments high energy high frequency focused beams of ultrasonic energy are used to heat and destroy diseased tissues. In the event that cavitation approaches to cleaning the TM may not be forceful enough to treat some patients, higher doses of energy might be required to ablate some of the finer meshes of the TM.

Intersecting Nodes.

In some embodiments, the approaches to stimulating the TM disclosed herein utilize beams of acoustic energy applied by single or multiple transducers in contact with the eye. In the case of multiple transducer stimulation, the risk of burning or overheating any portion of the eye can be mitigated, for example, through the use of lower level stimulation from two sources and using the overlapping energies to coincide where the treatment is most needed. The nodes and anti-nodes of acoustic energy will reinforce or cancel each other out. The shifting of frequency and phase will further mix up exact loci of these nodes, evening out the effect over a specific area of the eye, and minimizing the risk of heat damage from energy produced by a single transducer.

Focused Ultrasound.

The transducers described herein may be designed to focus their beams onto a localized area beneath the surface of the eye, and so to produce a cleaner 'intersection' of their energies. In addition, focused ultrasound beams may controlled and monitored at sub-corneal distances.

Tsunami Wave Migration of Acoustic Energy.

A tsunami in the ocean originates when there is an up or down-thrust of the earth's crust somewhere in the center of an ocean. This initiates a wave of energy that moves extremely rapidly away from the epicenter of the seismic event toward the shores of the ocean. As this wave travels at extremely high speeds through deep water, it begins to slow as shallower depths are reached. Amplitude (wave height) increases but overall energies are diminished somewhat by attenuation of acoustic energies by the medium and its surrounding confines. In other words, most of the energy of the earthquake is translated into violent wave activity at the perimeter of its shores.

This phenomenon may explain the positive results of lowered IOP shown by most patients who have undergone phacoemulsification (or phaco) of the cataract.

"Tsunami wave," as used herein, describes waves migrating from the epicenter of a fluid filled basin that is shallower at the edges than at the center. The anterior chamber of the eye is filled with fluid and has much the same shape as a shallow sea. Topical stimulation of the cornea here will send a wave migrating outwards to the edges of the corneal limbus, and may be used to supplement or reinforce the energies supplied topically to that area. The transducer arrays described herein can be designed to create a wave in the center of the anterior eye; stimulation at that point is referred to herein as "topical axial transducer stimulation".

Fourier Wave Transformation and Mixing.

In some embodiments disclosed herein, frequencies can be mixed and applied through the same transducer. This facilitates the application of a rolling 'massage' from lower frequencies to the solid portions of the TM while at the same time stimulating fluid flow, phagocytosis, or cavitation cleaning of the TM with higher frequencies applied by the same or nearby transducers. In some embodiments, each frequency of sound originates with a variety of phases, amplitudes (intensities) or points of origin.

Monotonic use of single-frequency sound offers the least attractive strategy for treating glaucoma. Multiple frequencies mixed together and multiple strategies for massaging the layers of TM, the streaming of fluids out of the anterior eye, stimulation of phagocytosis, ultrasonically cleaning the TM using principles of cavitation, or outright ablation of densely packed debris, are all strategies using sound, where the requirement of frequency and energy are different. The methods and devices disclosed herein provide an approach to the use of acoustic energy that can be custom fitted to the specific needs of individual glaucoma patients.

Frequency Induced Phagocytosis.

As most cells in the human body respond to vibration at some frequency, such as bone cells for bone repair, bone marrow for immune system support, or muscle cells for the alleviation of pain and stiffness, a regularly applied therapy of appropriate frequencies can enhance the rate of phagocytosis (breakdown of cellular debris) by the layers of the TM.

Real Time Imaging and Feedback.

Whenever sound energy is introduced to the body as a pulse or burst or a continuous wave, there is an opportunity to measure the reflected waves off various layers of tissue in the body and this can be done within the same transducer. This is the basic concept behind ultrasonic imaging. In same embodiments, the methods and devices disclosed herein comprise a diagnostic and/or feedback component, for example as part of the same device or transducer used to apply the therapeutic frequency stimulation, or as a separate component. Such components may measure sound reflection (echoes) from the interior of the eye or may utilize sonography.

Safety Precautions for Medical Ultrasound

"To date researchers have not identified any adverse biological effects caused by ultrasound even though three million babies born each year have had ultrasonic scans in utero." (Diagnostic Ultrasound Safety, a summary of the technical report "Exposure Criteria for Medical Diagnostic Ultrasound: Criteria Based on all Known Mechanisms" issued by the National Council on Radiation Protection and Measurements, p. 1.) This being said, the introductions of energies that produce cavitation or other physical effects of fluids in an area such as Schlemm's canal, or the angle of the eye, must take into consideration and minimize or diminish negative effects of such energy on living tissues. While it remains unclear whether there are any long-term effects of the diagnostic ultrasound in use today, scientists do know from laboratory studies that ultrasound at high intensities creates immediate effects at the time of exposure.

Hazards to fragile liquid filled cells are also somewhat unknown: "When ultrasound passes through liquid it causes a sort of stirring action called acoustic streaming. As the acoustic pressure of the ultrasound increases the flow of liquid speeds up. This stirring action, in theory, could occur in fluid filled parts of a patient's body, such as blood vessels, the bladder, or amniotic sac [or Schlemm's canal]. In experiments with animals, when streaming of the liquid comes near a solid object, shearing can occur, and this can damage platelets and lead to abnormal blood clotting (thrombosis)." [Ibid, page 5]

Transducer Arrays

Sound energy can be delivered to the eye using one or more transducers. Non-limiting means for delivering sound energy include (i) direct application of a single frequency; (ii) amplified mixing of different frequencies, where different waveforms are mixed and applied though the same transducer; (iii) multiple transducer—standing wave nodal stimulation, which uses standing wave interference and targeted sonic stimulation utilizing nodes and anti-nodes; and (iv) multiple transducer oblique angle waveform mixing, which uses the eye anatomy to cause waves from different sources to intersect.

The methods and devices of the present invention may contain arrays of multiple sonic and ultrasonic transducers of variable frequency, phase and amplitude. The transducers may be arranged in any desired configuration.

In some embodiments of the methods and devices disclosed herein, sound energy is applied as radial topical stimulation, topical axial stimulation or a combination thereof. As used herein, "radial topical stimulation" means stimulation at the surface of the eye in the vicinity of Schlemm's canal or the TM with an array of multiple transducers for delivery of sound energy of variable frequency, phase and amplitude to a region of the corneal Embus (see, for example, FIGS. 2, 3, 4 and 5). As used herein, "topical axial stimulation" means application of sound energy directly to the front of the cornea (see, for example, FIGS. 4, 5, 8C, 12, 13, 14, 15, 27 and 28). Topical axial stimulation takes advantage of the shape of the volume of fluid in the anterior chamber and utilizes a 'tsunami wave' (see FIGS. 4 and 5) to unleash sound energy that will ripple to the perimeter of the anterior chamber and the TM. The physics of propagation through fluid dictates that amplitudes rise as the waves approach the shallow circumference of a fluid body (FIG. 10C). Topical axial stimulation can be applied to supplement the energy applied topically via radial topical stimulation over the corneal limbus. Combined radial topical stimulation and axial corneal stimulation has the advantage of combining waveforms converging from different directions and uses multiple transducers located at different positions on the surface of the eye. In some embodiments, such a wave can be a low frequency burst designed to clear the TM of particles broken up by much higher frequencies, or be an attenuated high frequency wave designed to supplement the power of radial topical stimulation. Preferably, the methods and devices disclosed herein will use the lowest wattages and sound frequencies possible, thus minimizing the amount of energy introduced to the eye, and confining the focus of the energy to the areas targeted.

Examples of target areas of the eye to which treatments will be focused are the TM and the Schlemm's canal (FIGS. 1, 2 and 3). These areas of the eye are very close (approximately 0.5 millimeters) below the surface of the corneal limbus, and the surface of the cornea, and the sclera, in the area where they meet at the corneal angle is easily burned, and it is therefore necessary to introduce the energy to the surface at a level to avoid burning (the "threshold energy" level), for example by preventing two or more beams from sufficiently combining or focusing to produce an undesirable result such as burning. The devices disclosed herein use various combinations of methods to ensure the subsurface energy threshold in a confined area are enough to deliver an appropriate level of energy to treat the eye, but not to burn the eye. For example, this can be accomplished by focusing each individual transducer beam through the shaping of the transducer surface itself, coordinating output frequency and phase of each transducer so that the net sum of wave energies converges on the target area, using a specially machined surfaces on the transducers so as to introduce sound energy at an oblique angle to a surface of the eye, e.g., the corneal limbus, or aiming the beams so that there is a small area of overlap between them and adjusting threshold energy for the combined beams in this area so that energies elsewhere avoid the negative side effects of burning.

In some embodiments, the methods and devices disclosed herein comprise two or more transducers acting in concert to apply a frequency product (FIGS. 6, 9 and 10). As used herein, a "frequency product" (or "FP") is a combination of the same or different sonic or ultrasonic frequencies, with adjustments to phase, amplitude and duration. In some embodiments, combinations of sound energy can be learned and stored by the devices disclosed herein.

In some embodiments, the transducer arrays may vary in iteration according to one or more parameters such as cost requirements, lightness/size, distance between adjacent transducers, output energy level and frequency or overall device design. For example, the transducer arrays set into the glaucoma contact lens, described in Example 3 below, will preferably be designed so as to facilitate the incorporation of the transducers onto or into the contact lens, such as transducers constructed of thin-film or micro-machined transducers with a thickness of less than about 1 millimeter.

The shape and positioning of the transducers in the arrays may be designed as desired. In some embodiments, the transducers may have any desirable shape, such as round, either circular, oval, or representing a section of a circle or an ellipse, square, rectangular, trapezoidal, or crescent-shaped. In some embodiments, the transducers may be arranged or positioned as an array, such as a linear array, annular array, grid array or radial array. Arrangements of transducers may be two-dimensional or three-dimensional.

In some embodiments, transducer thicknesses may be sized and tuned to their natural resonant frequencies (half the wavelength) or be of variable frequency design as desired. The output to the transducers may be pulsed as single or multiple waves, or continuous, and combined single or multiple frequencies as desired, for example based on a patient's overall therapeutic program prescribed by a physician.

Surface and Design of Transducers and Transducer Arrays

Transducers may be constructed of different materials, and be of various sizes, conducive to the design and desired use of a device. For example, micro-machined, or thin film transducers will be the technology of choice for the glaucoma contact lens described in Example 3, however the other devices may use a variety of transducer types.

The focusing of transducer energy via a phased array may occur through a variety of designs of the individual transducers themselves. The surface of a transducer in contact with the eye (the 'feet' or 'contact surfaces' of the transducer) may have any desired shape, such as flat, concave or convex. In some embodiments, such surface is micro-machined flat, concave or convex and may include a set of fresnel ridges (angles cut into the transducer face) (FIG. 9) to facilitate a directionality of transducer energy. In some embodiments, arrays of transducers may have individual transducers set at angles different from each other to facilitate the focusing of transducer energy (FIG. 3). For example, two adjacent annular ring transducers may be angled so that their energies coincide or intersect just below the surface of the eye.

Heat Dispersing Couplant and Dispensing Mechanisms

In some embodiments, a material (such as a liquid) that facilitates the transmission of sound energy from the transducer into the eye (referred to as a couplant) is supplied to the interface of the face of the transducer or transducer array and the surface of the eye. In some embodiments the couplant is biocompatible. In some embodiments, the couplant is heat dispersing. The design and selection of the couplant may be determined by factors such as the amount of heat energy to be delivered, the solubility of the couplant by human tears, the ability of the couplant to be absorbed by tear ducts and broken down in lymph, and whether the density of the couplant is suitable for introducing sound energy into the cornea and/or corneal limbus of the eye.

Couplant may be applied or dispensed to the face of a transducer or transducer manually (such as by hand prior to using a device). Alternatively, a device can be designed such that couplant is automatically supplied as needed to the face of a transducer or transducer array and/or to the surface of the eye that is contacted by a transducer or transducer array. This may be accomplished in various iterations via a number of mechanisms (FIGS. 8D and 8E), for example, by extruding couplant from a dispensing mechanism on or in the device, such as an opening or slots or holes located, for example, in a rotor or adjacent to a transducer or transducer array, or by means of a spray onto a confined area of the eye. In some embodiments, a couplant mixture can be produced by mixing a non-Newtonian fluid with artificial tears. Such a mixture would behave much as tears do except when subjected to shear stress at a very high frequency, at which time the couplant viscosity would increase due to its dilatant properties. Such a fluid could be engineered to biodegrade in a safe and sanitary manner for the eye.

Power to Transducers and Transducer Arrays

The devices disclosed herein are powered electrically. Electric power may be supplied by any source or combination of sources, including but not limited to, electric mains, battery, capacitors or other power supplies. In some embodiments, the power source is wireless. In some embodiments, the power source is rechargeable. For example, the In-Clinic Device (see Example 1 and FIG. 11) and Hand-held Physician Device (see Example 5 and FIG. 24) may be powered by electric mains and a separate power supply, and the Glaucoma Glasses (see Example 2 and FIGS. 13-15) and Sonic Frequency Glaucoma Glasses (see Example 7 and FIGS. 27-28) may be plugged to the electric mains, or powered by an optional battery and power supply.

In some embodiments, the Transparent Battery Contact Lens (see Example 3 and FIGS. 19-20) may be powered by an internal transparent or opaque battery, storage capacitors, or by separate wireless power supplied by a special set of glasses worn by the user that conveys the power to the contact lens either through magnetic field induction, by radio frequency, or by a laser beam.

EXAMPLES

Illustrative embodiments of the methods and devices disclosed herein are provided in the following non-limiting examples.

Example 1

In-Clinic Device

The In-Clinic Device, as described in this Example and illustrated in FIGS. 11 and 12, could be used as an initial assessment to determine the treatability of a particular patient's glaucoma prior to prescription of other treatment methods and devices. This device can be designed to have the following features: immediate real time physical feedback, documentation of frequencies applied, where and how long (frequency products), patient specific treatment records, repeatability of treatments, variation of frequencies applied and mixes of frequencies generated, precision of application and re-application of sound energy, and custom software to monitor treatment, analyze feedback and record treatment. It is expected that this device initially would require the use of a physician, but later could be administrated by clinic technicians under prescription from a physician.

An In-Clinic Device can have a transducer array fitted to a mounting block with a surface matching the curvature of the corneal limbus of the eye (a topical radial transducer array). The transducer array can be mounted to a rotor, with a skirt designed to conserve and dispense heat dispersing couplant. This rotor-driven transducer array can be fitted to a gimbal unit to provide suspension and positive fitting of the array against the surface of the eye. The powering motor can be driven by a digital positioning system for sweeping the array around the radius of the corneal limbus according to any prescribed treatment program. The unit can include an automatic shut-off whereby the patient eye is scanned visually by a camera or laser in the unit and when the eye strays out of position relative to the transducer unit, power is immediately cut. When the patient's eye moves back on target, so that the target circumference of the corneal limbus is directly beneath the transducer array, treatment is resumed. In addition the rotor unit supports the addition of a topical axial transducer array which is fitted to the front of the cornea (a topical axial transducer array). The transducer array can convey wave energy from the anterior center of the eye to the periphery of the anterior chamber and to the edges of the TM.

The In-Clinic Device can include a positive positioning patient headrest, and collimated target optics to allow the patient to fixate the eye on a target, and concurrently allow the physician to view into the anterior chamber of the eye even when the topical radial transducer is in place and at work.

Both transducer arrays may be designed to produce a frequency product, that is a combined effect of focused, phased, and frequency modulated frequencies from multiple sources. The driving frequencies for each transducer in both arrays, can be produced by a control unit that is controlled by a computer, with software that allows the physician to precisely determine which frequencies, what phase, what amplitudes, and what duration will be produced by each transducer in the array, and combining that with what movements of the rotor and the portion of the eye is to be swept by the device.

The In-Clinic Device described in this Example, with its powering computer and software, will allow for repeatable therapies, and accurate logs of what frequency products were applied.

Example 2

Glaucoma Glasses

A modified version of the In-Clinic Device, called Glaucoma Glasses (illustrated in FIGS. 7, 13, 14 and 15), features similar but lighter weight transducers mounted in a gimbal suspension system mounted to a set of eyeglass frames, or helmet, with positive positioning with respect to the patient's eyes. The glasses could run a programmed treatment entered by the physician for a period of time. The glasses can achieve the objective of supplying lower cost treatment to the patient without the supervision of a physician. Patients could come into the clinic to use these glasses as directed, such as for a prescribed number of hours per week. It is expected that such glasses could be designed and manufactured so that they could be used by the patient at home.

An important aspect of the Glaucoma Glasses is related to safety. While the introduction of high frequencies to the eye are not likely to be painful, there is the risk of discomfort to the patient. At all times the patient must be able to stop or cease the treatment process. Both the programming and the design of the glasses will allow for predictable interruptions.

The Glaucoma Glasses achieve the objective of supplying lower cost treatment to the patient without the supervision of a physician. Patients would come into the clinic to use Glaucoma Glasses for a prescribed number of hours per week and in time, when such machines can be produced economically, they may be leased to patients for use at home.

Example 3

Transparent Battery Contact Lens

The Transparent Battery Contact Lens, worn by the patient, will regularly stimulate the corneal limbus of the eye with ultrasonic stimulation designed to loosen or cavitate TM debris and facilitate the draining of fluid from the anterior eye. This device is a contact lens constructed of multiple polymer layers. These layers can contain any or all of the following elements:

An exterior Bipolar Tear Layer to facilitate a layer of tears and movement of the eyelid.

A Photocell Layer, covering the iris of the wearer, and optionally colored similar to the iris of the wearer. The edge of this layer can be colored white to match the sclera of the wearer and the transducer arrays located at the edge of the lens. The photocell layer may contain a LED emitting infrared or other light radiation for the purposes of communicating with the Wireless Power Transfer (WPT) glasses (described in Example 4 below).

An Induction Coil Layer if the device uses induction WPT.

A Capacitor/Transparent Battery Layer—this layer is expected to make up most of the thickness of the lens and is diopter adjusted to the patient.

A UV Filter Layer over the pupil region may be combined with one or more of the other mentioned layers, as this will provide sunglasses-like protection to the eye, and enable the user to be in the presence of bright sunlight without compromising power from the Photocell Layer.

A Powering Circuit Layer containing the integrated circuitry for powering the device, charging its internal batteries/capacitators and for communicating with a WPT source of power.

A Transducer Array Layer contains the micro-machined thin-film transducers located on the periphery. This layer may contain a dispensing mechanism, such as pouches or sacks, containing small amounts of couplant that can be extruded to the eye surface via transducer energy. This couplant may be composed of a catalyst and a non-Newtonian fluid that responds to ultrasound stimulation by increasing the viscosity of the tear layer.

A Corneal Contact Layer is a bi-polar plastic layer that comes into contact with the surface of the eye and is much the same composition and material as other contact lenses known in the art.

The contact lens will supply ultrasonic stimulation and bursts of cavitation level energy to discrete areas just above the TM on a regular basis.

The contact lens can contain an operating system stored in on-board ROM chip and programmed by a Transparent Battery Contact Lens management device operated by a physician or clinic. This can be used to set the program for the Transparent Battery Contact Lens, as prescribed by the physician according to the type and severity of glaucoma suffered by the patient. The program parameters, are fed from this device into the contact lens, after which it can be worn and taken home by the patient.

The Transparent Battery Contact Lens can keep a record in its memory of the therapies administered to the patient. These are downloaded by the Transparent Battery Contact Lens management device upon return to the clinic. The Transparent Battery Contact Lens can be configured to communicate directly with an application in the patient's cellphone or PDA and so downloads therapy history to the clinic.

The Transparent Battery Contact Lens can have variations regarding use and sources of power. For example, the contact lens could use a transparent rechargeable battery and photocells for charging. Another example uses laser WPT (see Example 4 below) to recharge the contact lens from a special set of glasses harboring a small laser beam and control electronics housed in the eyeglass frame. Another example uses induction WPT to induce regenerative power from a coil in the eyeglass lens or eyeglass frame to a coil located in the Transparent Battery Contact Lens. Both forms of WPT for recharging of the Transparent Battery can use an infrared (IR) or radio frequency (RF) feedback circuit or both. The RF circuit, though it may employ some level of signal encoding for security purposes, is potentially vulnerable to RF interference from the environment, whereas an RF signal confirmed by an infrared signal from a LED within the device could increase the safety of the contact lens.

The Transparent Battery Contact Lens is powered by a transparent internal battery. This battery can be rechargeable, such as by means of a solar cell array which composes the portion of the contact lens that covers the iris of the patient, and can be colored to match the iris color of the patient. The charging electronics are located in the circuit layer of the lens and handle the recharging of the device in a manner similar to other rechargeable solar cell powered devices. The circuitry interacts with the transducer array controls portion of the device to ensure that enough power is present before beginning a series of energy bursts to the transducer arrays.

The Transparent Battery Contact Lens is expected to use frequency induced phagocytosis and undulation massage of the TM as the primary therapeutic method. The contact lens can use topical axial frequencies from low to high ultrasonic. The total wattage at the cornea can be around 1-40 watts with radial phased array frequencies of 20 kilohertz to 200 kilohertz/1 microwatt to 5 watts at each transducer. For time dependent therapy, frequencies can be delivered as bursts for periods of around 0.1-30 seconds each.

Example 4

WPT Transparent Battery Contact Lens

Another iteration of contact lens device uses Wireless Power Transfer (WPT) to supply power to the Transparent Battery Contact Lens (FIG. 21). This device may be useful in areas without adequate sunlight, or for patients requiring higher levels of therapeutic stimulation.

One embodiment of the WPT Transparent Battery Contact Lens uses laser wireless power transfer to recharge the device from a special set of glasses harboring a tiny laser beam and control electronics beside each eye in the eyeglass frame. A second embodiment uses induction WPT to induce regenerative power from a coil in the eyeglass lens or eyeglass frame to a coil located in the Transparent Battery Contact Lens. Both forms of WPT for recharging of the Transparent Battery Contact Lens require the use of an Infrared (IR) or radio frequency (RF) feedback circuit. A Fractal Antenna Layer to transmit and receive RF signals to and from WPT Glasses used for charging.

Some iterations could require both. The RF circuit, though it may employ some level of signal encoding for security purposes, is potentially vulnerable to RF interference from the environment, whereas an RF signal confirmed by an Infrared signal from a LED within the device would increase the safety of the device.

Example 5

Wireless Power Transfer (WPT) Glasses

As described in Example 4, Wireless Power Transfer (WPT) to a contact lens may be accomplished via a set of specially designed set of WPT glasses (FIGS. 22 and 23). This device facilitates inductive power coupling or laser power coupling with the recharging circuits in the Transparent Battery Contact Lens. These glasses can be worn by the patient during times of day when therapy is called for. The glasses may or may not have corrective lenses for the patient's vision, allowing the patient to work, read, drive or watch a movie during periods of therapy. The wirelessly powered contact lenses may combine any or all of the features described herein for power transmission, generation, storage, or recharging.

For the induction rechargeable Transparent Battery Contact Lens, coils in the WPT Glasses frames (or within the glass lenses themselves), pass an alternating current which forms an oscillating magnetic field which induces an alternating current in the receiving coils of the Transparent Battery Contact Lens. This alternating current may be rectified and used immediately or stored by a capacitor, battery, or series of capacitors or batteries in the device. Whether energy is stored temporarily or used directly, it can be used to power the control circuits and transducer arrays of the Transparent Battery Contact Lens.

For the laser rechargeable Transparent Battery Contact Lens, another iteration of the WPT glasses uses a short burst from a low-power laser to beam energy to the photocell layer of the Transparent Battery Contact Lens. Microbursts of laser energy at low levels occur regularly to test the location of the charging photocell on the contact lens with respect to saccade movements of the eye. Positive feedback via RF or IR provides real time position data to the charging device. The WPT Glasses 'know' when the eye is in position to receive a charging burst of laser energy. If the feedback loop is compromised, paused, or stopped, no energy is transferred.

The human eye moves extremely quickly in bursts of movement termed saccades. The peak angular speeds of the eye during a saccade reaches up to 900 degrees per second in humans. Saccades responding to an unexpected stimulus normally take about 200 milliseconds (ms) to initiate, and then last from about 20-200 ms, depending on their amplitude. 20-30 ms is typical in language reading. Because the eye can rapidly turn away from a fixed locus, the response time of the laser start-and-stop electronics for the WPT Glasses must be equally rapid. If response times are short enough, and the charging laser is of an amplitude that would require a significant time to harm the eye, the eye may be safeguarded by the use of a feedback circuit as described herein. Software for controlling the charging mechanism may be designed to learn the patterns of saccade movement of the patient eye, boosting charging efficiencies of the device. In other iterations, the movement of the eye may be sensed by a photocell array in the lens. Once movement is sensed, power is terminated. The eye is protected by real time positive feedback from the charging process, to prevent directing laser energy into the eye. The charging bursts may occur through the same or separate lasers, with either or both lasers projecting their beams in the same direction. If separate lasers, one laser may be dedicated to providing location information to the device, for example the contact lens. Once the target is 'located' and the photocell is appropriately angles, the charging laser produces a burst of energy. If the charging burst commences, but feedback is not received during the time of the charging burst, the charging burst is terminated.

Laser sends out microburst of low-level laser energy.
If it is received, the device sends repetitive coded signals on an RF frequency and/or IR pulse back to the charging glasses.
The charging glasses then send forth a burst of charging energy for as long as the coded signals indicate that the eye is in position.
The instant the RF feedback loop is interrupted the charging laser switches off.

In some embodiments, a light (for example, a low level LED light) may be included as part of the device that indicates to the user when the power has decreased below a recommended or acceptable level. The user can then stare at fixed points without moving the eye, so as to speed up the re-charging process of the device. Such feedback elements may also communicate other device parameters to the user.

The laser source can be located within the eyeglass frame at the outside of the eye, and the beam is directed at an oblique angle towards the surface of the Transparent Battery Contact Lens where the photocell array is located. The RF/IR feedback loop can continuously monitor the location of the device. Bursts of power may be in the order of 1-200 milliseconds. Bursts for low bursts for purpose of feedback on position monitoring of the device are much shorter and at a tiny fraction of the energy of the main charging laser.

Example 6

Physician Handheld Transducer Array

A transducer array as described above for the In-Clinic Device could also be fashioned into a hand-held device (FIGS. 24, 25 and 26). The handheld device would allow a physician to directly apply sound energy stimulation to a portion of the glaucoma patient's eye. Similar to the In-Clinic Device, the Physician Handheld Transducer Array allows the removal and replacement of a variety of transducer array heads. There are three illustrative transducer arrays that may be fitted to this device, depending on which area of the eye the array will contact when fitted to the eye, for example, arrays that have a spheroid surface for fitting to the corneal sclera (the white portion of the eye), arrays that have a complex dual spheroid surface for fitting to the corneal limbus (the junction of the cornea with the white of the eye), or arrays that have a spheroid surface fitted to the front of the cornea. The Physician Handheld Transducer Array combines a single interchangeable transducer array with a handheld unit. It can be designed to receive power and control from the same attached PC with dedicated software as the In-Clinic Device, except that there is no rotor, or automatic rotation machinery. The unit is designed to be handheld, or optionally mounted to the gimbal system for rotation by the physician.

Example 7

Sonic Frequency Glaucoma Glasses

As illustrated in FIGS. 27 and 28, two high sonic frequency transducers stimulate the patient's closed eyelids, while a pair of larger MF Sonic transducers apply debris clearing energy from the patient temples. This device would employ frequency induced phagocytosis and liquefaction. The sonic frequencies used in this Example are designated "HF Sonic" to mean high-pitched sonic frequencies, which are audible, as opposed to "HF" which stands for high frequency ultrasonic frequencies. "MF Sonic" means mid-range audible energies.

Reference throughout this specification to "one embodiment," "some embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A multi-layer contact lens that delivers sound energy to a mammalian eye, comprising:
    a transducer and circuit layer having a first plurality of sound energy generating transducers and a second plurality of sound energy generating transducers both electrically interconnected to a system power circuit via a circuit bus wherein the first plurality of sound energy generating transducers, the second plurality of sound energy generating transducers, the system power circuit and the circuit bus are all supported by the transducer and circuit layer;
    a battery layer abutting the transducer and circuit layer supporting a transparent rechargeable battery, the transparent rechargeable battery electrically interconnected to the first plurality of sound energy generating transducers, the second plurality of sound generating transducers and the system power circuit; and
    a thin-film photocell layer supporting photocells that are electrically interconnected to both the transparent rechargeable battery and the system power circuit,
    wherein an optically transparent central region is configured to overlie a pupil of the mammalian eye of each of the respective transducer and circuit layer, the battery layer and the thin-film photocell layer and an exterior region is configured to overlie an iris of the mammalian eye, and
    wherein the first plurality of sound energy generating transducers are supported only by a peripheral region of the exterior region of the transducer and circuit layer and the second plurality of sound energy generating transducers are supported only by the exterior region between the first plurality of sound generating transducers and the optically transparent central region.

2. The multi-layer contact lens of claim 1 wherein the first plurality of sound energy generating transducers are within a tension ring that expands and contracts when the first plurality of sound generating transducers are energized.

3. The multi-layer contact lens of claim 2 wherein the tension ring is disposed between the transducer and circuit layer and the battery layer.

4. The multi-layer contact lens of claim 1 wherein an antenna is disposed between two of the respective transducer and circuit layer, the battery layer and the thin-film photocell layer.

5. The multi-layer contact lens of claim 4 wherein the antenna is a radio-frequency fractal antenna supported by an optically transparent antenna layer.

6. The multi-layer contact lens of claim 1 wherein the transparent rechargeable battery is supported by the central region of the battery layer and delivers bursts of power to both the first plurality of sound energy generating transducers and to the second plurality of sound energy generating transducers.

7. The multi-layer contact lens of claim 6 wherein the transparent rechargeable battery is selected from the group consisting of lithium ion and vanadium oxide graphene.

8. The multi-layer contact lens of claim 6 wherein the photocells are supported by the exterior region of the thin-film photocell layer.

9. The multi-layer contact lens of claim 8 wherein the photocells are copper indium gallium diselenide (CIGS).

10. The multi-layer contact lens of claim 1 wherein the first plurality of sound energy generating transducers and the second plurality of sound energy generating transducers are independently selected from the group consisting of PZT (lead-zirconium titanate) thin film high frequency transducer PMUT (piezoelectric micromachined ultrasonic transducers), capacitive micromachined ultrasonic transducers (CMUT) and other micromachined or thin film technology.

11. The multi-layer contact lens of claim 10 wherein each transducer of the first plurality of sound energy generating transducers and the second plurality of sound energy generating transducers has a power of between 1 microwatt and 5 watts and a frequency of between 20 kHz and 200 kHz.

12. The multi-layer contact lens of claim 10 wherein an optically transparent corneal contact layer abuts the transducer and circuit layer on a side opposite the battery layer.

13. The multi-layer contact lens of claim 12 wherein a couplant filled suction zone is disposed between the optically transparent corneal contact layer and the mammalian eye.

14. The multi-layer contact lens of claim 12 wherein an outer film tear layer abuts the thin-film photocell layer on a side opposite the transparent flexible battery layer, the outer film tear layer facilitating a layer of tears and movement of the eyelid.

15. The multi-layer contact lens of claim 14 wherein one or more of the respective transducer and circuit layer, the battery layer, the thin-film photocell layer, the corneal contact layer and the outer film tear layer is color tinted.

16. The multi-layer contact lens of claim 14 wherein one or more of the respective transducer and circuit layer, the battery layer, the thin-film photocell layer, the corneal contact layer and the outer film tear layer is coated with an ultraviolet protection.

* * * * *